US006392016B1

(12) United States Patent
Lurquin et al.

(10) Patent No.: US 6,392,016 B1
(45) Date of Patent: May 21, 2002

(54) ISOLATED PROTEIN MOLECULES WHICH ARE MEMBERS OF THE MAGE-B FAMILY

(75) Inventors: Christophe Lurquin; Francis Brasseur; Thierry Boon-Falleur, all of Brussels (BE)

(73) Assignee: Ludwig Institute for Cancer Research, New York, NY (US)

(*) Notice: Subject to any disclaimer, the term of this patent is extended or adjusted under 35 U.S.C. 154(b) by 0 days.

(21) Appl. No.: 09/443,077

(22) Filed: Nov. 18, 1999

Related U.S. Application Data

(60) Division of application No. 08/846,111, filed on Apr. 25, 1997, now Pat. No. 6,017,705, which is a continuation-in-part of application No. 08/658,578, filed on Jun. 5, 1996, now Pat. No. 5,759,783, which is a continuation-in-part of application No. 08/403,388, filed on Mar. 14, 1995, now Pat. No. 5,587,289.

(51) Int. Cl.$^7$ ................................................. C07K 1/00
(52) U.S. Cl. ......................................................... 530/350
(58) Field of Search ................................. 530/350, 300; 536/23.5

(56) References Cited

PUBLICATIONS

Anichini, et al, "Cytotoxic T Cells Directed to Tumor Antigens Not Expressed on Normal Melanocytes Dominate HLA–2.1 Restricted Immune Repertoire To Melanoma," J. Immunal 156: 208–217 (1996).

Coulie, et al, "A mutated intron sequence codes for an antigenic peptide recognized by cytolytic T Lymphocytes on a human melanoma," Proc. Natl. Acad. Sci. USA 92: 7976–7980 (1995).

DeSmet, et al, "Involvement of two Ets binding sites in the transcriptional activation of the MAGE1 gene," Immunogenetics 42: 282–290 (1995).

Gaugler, et al., "Human Gene MAGE–3 Codes For an Antigen Recognized on a Melanoma by Autologous Cytolytic T Lymphocytes," J. Exp. Med. 179: 921–930 (1994).

Imai, et al, "Sequence Analysis of the MAGE gene family encoding tumor rejection antigens," Gene 160: 287–290 (1995).

McCurdy, et al, "MAGE Xp–2: A Member of the MAGE Gene Family Isolated From An Expression Library Using Systemic Lupus Erythematosus Sera," Mol Genet and Metab. 63: 3–13 (1998).

Muscatelli, et al, "Isolation and Characterization of a MAGE gene family in the Xp21.3 region," Proc. Natl. Acad. Sci USA 92: 4987–4991 (1995).

Traversari, et al, "A Nonapeptide Encoded By Human Gene MAGE–1 Is Recognized as HLA–A1 by Cytolytic Lymphocytes Directed Against Tumor Antigen MZ2–E," J. Exp Med. 176: 1453–1457 (1992).

Van den Eynde, et al, "A New Family of Genes Coding For An Antigen Recognized By Autologous Cytolytic T Lymphocytes on a Human Melanoma," J. Exp. Med. 182: 689–698 (1995.

Van der Bruggen, et al, "A peptide Encoded By Human Gene MAGE–3 and presented by HLA–A2 induces cytolytic T lymphocytes that recognize tumor cells expressing MAGE–3," Eur. J. Immunal 24: 3038–3043 (1994).

Van der Bruggen, et al, "A Gene Encoding An Antigen Recognized By Cytolytic T Lymphocytes on a Human Melanoma," Science 254: 1643–1647 (1991).

Zakut, et al, "Differential Expression of MAGE–1, 2, and –3 Messenger RNA In Transformed and Normal Human Cell Lines," Canc. Res. 53: 5–8 (1993).

Lurquin et al. Genomics (1997) 46: 397–408.*
Dabovic et al. Mammalian Genome (1995) 6: 571–580.*

\* cited by examiner

*Primary Examiner*—Lisa B. Arthur
(74) *Attorney, Agent, or Firm*—Fulbright & Jaworski, LLP

(57) ABSTRACT

The invention relates to members of the MAGE-B family of nucleic acid molecules. These molecules differ from the previously described MAGE nucleic acid molecules in that members of the MAGE-Xp family do not hybridize to the previously identified MAGE sequences. Further, the members of the MAGE-B family are found on the Xp arm of the X chromosome rather than on the Xq chromosome, as was the case with the previously identified MAGE genes.

7 Claims, No Drawings

SEQUENCE LISTING (1) GENERAL INFORMATION:

(iii) NUMBER OF SEQUENCES: 18

(2) INFORMATION FOR SEQ ID NO: 1:

(i) SEQUENCE CHARACTERISTICS:
      (A) LENGTH: 1866 base pairs
      (B) TYPE: nucleic acid
      (C) STRANDEDNESS: single
      (D) TOPOLOGY: linear (xi) SEQUENCE DESCRIPTION: SEQ ID NO: 1:

```
GAGTGTTGCA ACTGGGCCTG GCATGTTTCA GCGTGGTGTC CAGCAGTGTC T CCCACTCCT     60

TGTGAAGTCT GAGGTTGCAA AAGGACTGTG ATCATATGAA GATCATCCAG G AGTACAACT    120
```

```
CGAAATTCTC AGAAAACAGG ACCTTGATGT GAGAGGAGCA GGTTCAGGTA A ACAAAGGGC        180

GAGGACCCGA GCGAGCTTAA GGCCAGTGGG GTGCAGCGTC TGGTCAGCCG A GGGTGAATT        240

CTCAGGACTG GTCGGGAGTC AAGGTGCCAC ATCTCCTGCC TTTCTGCTCA C TTTCCTGCC        300

TGTTTTGCCT GACCACAGCC ATCATGCCTC GGGGTCAGAA GAGTAAGCTC C GTGCTCGTG        360

AGAAACGCCG CAAGGCGCGA GAGGAGACCC AGGGTCTCAA GGTTCGTCAC G CCACTGCAG        420

CAGAGAAAGA GGAGTGCCCC TCCTCCTCTC CTGTTTTAGG GGATACTCCC A CAAGCTCCC        480

CTGCTGCTGG CATTCCCCAG AAGCCTCAGG GAGCTCCACC CACCACCACT G CTGCTGCAG        540

CTGTGTCATG TACCGAATCT GACGAAGGTG CCAAATGCCA AGGTGAGGAA A ATGCAAGTT        600

TCTCCCAGGC CACAACATCC ACTGAGAGCT CAGTCAAAGA TCCTGTAGCC T GGGAGGCAG        660

GAATGCTGAT GCACTTCATT CTACGTAAGT ATAAAATGAG AGAGCCCATT A TGAAGGCAG        720

ATATGCTGAA GGTTGTTGAT GAAAAGTACA AGGATCACTT CACTGAGATC C TCAATGGAG        780

CCTCTCGCCG CTTGGAGCTC GTCTTTGGCC TTGATTTGAA GGAAGACAAC C CTAGTAGCC        840

ACACCTACAC CCTCGTCAGT AAGCTAAACC TCACCAATGA TGGAAACCTG A GCAATGATT        900

GGGACTTTCC CAGGAATGGG CTTCTGATGC CTCTCCTGGG TGTGATCTTC T TAAAGGGCA        960

ACTCTGCCAC CGAGGAAGAG ATCTGGAAAT TCATGAATGT GTTGGGAGCC T ATGATGGAG       1020

AGGAGCACTT AATCTATGGG GAACCCCGTA AGTTCATCAC CCAAGATCTG G TGCAGGAAA       1080

AATATCTGAA GTACGAGCAG GTGCCCAACA GTGATCCCCC ACGCTATCAA T TCCTATGGG       1140

GTCCGAGAGC CTATGCTGAA ACCACCAAGA TGAAAGTCCT CGAGTTTTTG G CCAAGATGA       1200

ATGGTGCCAC TCCCCGTGAC TTCCCATCCC ATTATGAAGA GGCTTTGAGA G ATGAGGAAG       1260

AGAGAGCCCA AGTCCGATCC AGTGTTAGAG CCAGGCGTCG CACTACTGCC A CGACTTTTA       1320

GAGCGCGTTC TAGAGCCCCA TTCAGCAGGT CCTCCCACCC CATGTGAGAA C TCAGGCAGA       1380

TTGTTCACTT TGTTTTTGTG GCAAGATGCC AACCTTTTGA AGTAGTGAGC A GCCAAGATA       1440

TGGCTAGAGA GATCATCATA TATATCTCCT TTGTGTTCCT GTTAAACATT A GTATCTTTC       1500

AAGTGTTTTT CTTTTAATAG AATGTTTATT TAGAGTTGGG ATCTATGTCT A TGAGCGACA       1560

TGGATCACAC ATTTATTGGT GCTGCCAGCT TTAAGCATAA GAGTTTTGAT A TTCTATATT       1620

TTTCAAATCC TTGAATCTTT TTTGGGTTGA AGAAGAAGAA AGCATAGCTT T AGAATAGAG       1680

ATTTTCTCAG AAATGTGTGA AGAACCTCAC ACAACATAAT TGGAGTCTTA A AATAGAGGA       1740

AGAGTAAGCA AAGCATGTCA AGTTTTTGTT TTCTGCATTC AGTTTTGTTT T TGTAAAATC       1800

CAAAGATACA TACCTGGTTG TTTTTAGCCT TTTCAAGAAT GCAGATAAAA T AAATAGTAA       1860

TAAATT                                                                  1866

(2) INFORMATION FOR SEQ ID NO: 2:

(i) SEQUENCE CHARACTERISTICS:
         (A) LENGTH: 461 base pairs
         (B) TYPE: nucleic acid
         (C) STRANDEDNESS: single
         (D) TOPOLOGY: linear (xi) SEQUENCE DESCRIPTION: SEQ ID NO: 2:

GCTGCGGCTG CGGGTGTTTC ATCCACAAAA TCTAAAAAAG GTGCCAAGAG C CACCAAGGT         60

GAGAAAAATG CAAGTTCCTC CCAGGCCTCA ACATCCACTA AGAGCCCAAG C GAAGATCCT        120

CTAACCAGGA AGTCAGGGTC GTTGGTGCAG TTCCTGTTGT ACAAGTATAA A ATAAAAAAG        180

TCCGTTACAA AGGGAGAAAT GCTGAAAATT GTTGGCAAAA GGTTCAGGGA G CACTTCCCT        240
```

GAGATCCTCA AGAAAGCCTC TGAGGGCCTC AGTGTTGTCT TTGGCCTTGA G CTGAATAAA      300

GTCAACCCCA ACGGCCACAC TTACACCTTC ATCGACAAGG TAGACCTCAC T GATGAGGAA      360

TCCCTGCTCA GTTCCTGGGA CTTTCCCAGG AGAAAGCTTC TGATGCCTCT C CTGGGTGTG      420

ATCTTCTTAA ATGGCAACTC AGCTACTGAG GAAGAGATCT G                            461

(2) INFORMATION FOR SEQ ID NO: 3:

(i) SEQUENCE CHARACTERISTICS:
        (A) LENGTH: 476 base pairs
        (B) TYPE: nucleic acid
        (C) STRANDEDNESS: single
        (D) TOPOLOGY: linear (xi) SEQUENCE DESCRIPTION: SEQ ID NO: 3:

ATCACTGCAA CTAACAAGAA AAAAGTATCC TTTTCATCCC CTCTTATTTT G GGGGCTACT        60

ATCCAGAAAA AGTCTGCTGG TAGGTCACGT AGTGCTCTCA AGAAGCCTCA G AGAGCACTA      120

TCCACCACTA CATCTGTAGA TGTTTCTTAC AAAAAGTCAT ACAAGGGAGC C AACAGCAAA      180

ATTGAGAAAA AGCAAAGCTT CTCTCAGGGT CTATCCTCCA CTGTGCAGTC T CACACAGAC      240

CCTCTAACCA TGAAGACAAA TATGTTGGTG CAGTTCCTGA TGGAAATGTA C AAGATGAAA      300

AAGCCCATTA TGAAAGCAGA TATGCTAAAA ATTGTCCAAA AAAGCCATAA G AATTGCTTC      360

CCTGAGATCC TTAAAAAAGC TTCTTTCAAC ATGGAGGTGG TGTTTGGTGT T GATTTAAAG      420

AAAGTTGATT CTACCAAGGA CTCCTATGTC CTTGTCAGCA AATGGATCT C CCCAA           476

(2) INFORMATION FOR SEQ ID NO: 4:

(i) SEQUENCE CHARACTERISTICS:
        (A) LENGTH: 687 base pairs
        (B) TYPE: nucleic acid
        (C) STRANDEDNESS: single
        (D) TOPOLOGY: linear (xi) SEQUENCE DESCRIPTION: SEQ ID NO: 4:

CATCACCTGC CCTTCTGCCT ACACTCCTGC CTGCTGTGCC TAACCACAGC C ATCATGCCT       60

CGGGGTCAGA AGAGTAAGCT CCGTGCCCGT GAGAAACGCC AGCGGACCCG T GGTCAGACC     120

CAGGATCTCA AGGTTGGTCA GCCTACTGCA GCAGAGAAAG AAGAGTCTCC T TCCTCTTCC     180

TCATCTGTTT TGAGGGATAC TGCCTCCAGC TCCCTTGCTT TTGGCATTCC C CAGGAGCCT     240

CAGAGAGAGC CACCCACCAC CTCTGCTGCT GCAGCTATGT CATGCACTGG A TCTGATAAA     300

GGCGACGAGA GCCAAGATGA GGAAAATGCA AGTTCCTCCC AGGCCTCAAC A TCCACTGAG     360

AGATCACTCA AAGATTCTCT AACCAGGAAG ACGAAGATGT TAGTGCAGTT C CTGCTGTAC     420

AAGTATAAAA TGAAAGAGCC CACTACAAAG GCAGAAATGC TGAAGATCAT C AGCAAAAAG     480

TACAAGGAGC ACTTCCCTGA GATCTTCAGG AAAGTCTCTC AGCGCACGGA G CTGGTCTTT     540

GGCCTTGCCT TGAAGGAGGT CAACCCCACC ACTCACTCCT ACATCCTCGT C AGCATGCTA     600

GGCCCCAACG ATGGAAACCA GAGCAGTGCC TGGACCCTTC CAAGGAATGG G CTTCTGATG     660

CCTCTACTGA GTGTGATCTT CTTAAAT                                          687

(2) INFORMATION FOR SEQ ID NO: 5:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO: 5:

TAAAAAAGGT GCCAAGAGCC AC                                              22

(2) INFORMATION FOR SEQ ID NO: 6:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 6:

TGAGGCCCTC AGAGGCTTTC                                                 20

(2) INFORMATION FOR SEQ ID NO: 7:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO: 7:

AGTCTGCTGG TAGGTCACGT A                                               21

(2) INFORMATION FOR SEQ ID NO: 8:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO: 8:

TCAGGAACTG CACCAACATA TTT                                             23

(2) INFORMATION FOR SEQ ID NO: 9:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 9:

AGGGATACTG CCTCCAGCTC                                                 20

(2) INFORMATION FOR SEQ ID NO: 10:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO: 10:

CAGGAACTGC ACTAACATCT TC                                              22

(2) INFORMATION FOR SEQ ID NO: 11:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 11:

GTGGTGTCCA GCAGTGTCTC                                                 20

(2) INFORMATION FOR SEQ ID NO: 12:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO: 12:

GTCAGATTCG GTACATGACA CAG                                             23

(2) INFORMATION FOR SEQ ID NO: 13:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO: 13:

AATGTGTTGG GAGCCTATGA T                                               21

(2) INFORMATION FOR SEQ ID NO: 14:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO: 14:

ATTATGTTGT GTGAGGTTCT TTCA                                            24

(2) INFORMATION FOR SEQ ID NO: 15:

(i) SEQUENCE CHARACTERISTICS:
        (A) LENGTH: 40352 base pairs
        (B) TYPE: nucleic acid
        (C) STRANDEDNESS: single
        (D) TOPOLOGY: linear (xi) SEQUENCE DESCRIPTION: SEQ ID NO: 15:

AAGCTTCAGA GTTGAGAGAC TAAGCCTATA ATGGAAAAGT GCTCTTAACT                 50

TTGGAGAAAA CTGGAAAGAA GCTCCACCAG GGGCAGCACT GGAAAGTGAC                100

TATGCTCTTG TCCCAGTGCA GATGAACACA GTGCAGAAAC TAGCTGCTTT                150

ATATACATTG TATCCAGTGA GCTTCGGAGA AATAAGGATG ATACTCCCTT                200

AAGAAGAAAT GATAAGAAGC CGCTGGGTAC TCTGCACTGG GCTGGAAGAG                250

TTAAGAGTCA ATTTCATTAA AAGGAGCATT CAAATTAGGC TATCATGTAC                300

ATAATTTGGC AAGCTCTAGG CAAGTTCTAG GTGTTTGGTG CTTGTTAAAT                350

TAATGAAAAT AAAGGTGATT TAGATGGAAG TGACACTGGG AGGGAAGGAA                400

GTTGTTAGTC CTTGACGCAA ATGCGTTGTG TTGCACCTAA ACTGGAGAAG                450

TCTACCTCAC ATTGAATAAT TTATCATTTA ATGGGGAAAT ATTACTTGAT                500

TTTTCGTGCT AATCTGCATT TTGGCTTATT GGGTTTTCTT TCTTCTAGAA                550

TGCTGCATAT TCTCTGACAT CTGTTGGATT AAGAAAAAGC AATCACAGTG                600

GGATGGGTGG TATCATCAAG TTAATCATAG GTAATAGCTG CCATGTTGAA                650

```
ACCTCAATAT GGGCCAAGTA TTGTGCCAGG TGCTTTACAT ACATTAACCA      700

CATTTCACCA ATTCCACAAG GAAGGGGCTT ATCAAACCTA TTTCACAGAT      750

GCAGAGCCTG AGGCTCACAG AGTTTAGTAA TGTGCCTGAG TTCACATAGC      800

TGGTAAGTGG CAGGGCTGAA ACCAGACCCC CAGTCTGGAT TAATCTACAT      850

CCCACACTGT TCCAGTCTTC CCATTCTGAG GCTAACCTCA TGTTGCTTCA      900

TTCATTTTTT CTCTCTATTT TTGAAAAATG TATCTCAGGC AATAAAAAGA      950

AGGACTCTGT GCCCATACTA CTGGGTCAAA TATATTCCCA GACCAATATG     1000

AATGCCAAAA TAAATGAGAG GCATAAATAA AAAAAAGAAA AATAGTACCT     1050

GGTGTCAATA CGTTCATCTA CACAAGCAAT ATCAGGTAAT CTCAAAAGAT     1100

CAGAAGCTCC CAAAATCATC CTGGACAGTC TCTTCCCTGT AGAAAATAAA     1150

TGTGTCAGAA CAGAATTTTC GTGAGAATCT AAGTCTAGCA AGATGGAAAA     1200

AATCAGCATG TTTTTTTCTC TGACAGCCCA CTACCTGTCC TGGAGCTTCT     1250

GCCTTGTGCT TCAGCTTCCC TATCTCACAT CACTCCCGGA ACACGGCTCC     1300

TTCTCTGCAA GGTTTGCAGT AGAAAAACTG GTCATGTTTG CAGGGATGTG     1350

ACATTTCCCA GAAAGCCTTT AATGAAAGAT GATCCCCAGT TCAGAGGACA     1400

TGGGAAACCA ATATCTCAGA ATATATGAGG TTATGCATAG ACTGACTCTC     1450

ATCTGCTCTC AGACCTAGAG AGCTCGAGAC AGAACTGTCA GGCTGAGCAT     1500

CCACTCATTT AATCTTCAGA CCTCTCATGG ACATGGCCTA AGAAGGTCAA     1550

CTTCATGTCA GTAGATGCAG TTCAGCCTCT GATAGATATG AACGTGAGGA     1600

CCCTGAATGA AGATGATGGA AGGACCCAGC CAGAACTGTG GGGTCCCAAA     1650

AAGTCCAGCT CAGGCTGTCA GCCCTTCAAA GTCCAGAACA GCCCTGGCTA     1700

AATGTAGCTC ACCACAACTT CCAGTTCAGA GGTCGGCAGA GGGTGAGTAC     1750

CTTGATCTGA TGGGAACAGC CTCAGGTCAG TGGAGGATGG AGTGCCCCAA     1800

GACTGGCCAG GTGTCATGGT GAGGACCCTG AAGAGAAATA AGAGAACTGT     1850

TATAGGACCA ACGAGTTTCT GTGTCAGCTG CAAAGTAACA GACCCACTAT     1900

AATAAAACAG CAAAGTTTGC AGCAAAGAGT TTAATGATTG CAGGGTGCCA     1950

AGTGAGGAGA TGAGAAGAGA CTCTCAAATT CATCTCCCCA AGGAGTTCTG     2000

GGCTGGGATT TGCAAGGAGA TCATGGAGGG CGAGGGGCTG GAGAACTGAG     2050

GTTGTTGATT CGTTGGGGTA AAGGGGATGA ATCATCAGA ATGTGGAAAC      2100

TGCGTTTTTT TTTTTTTAGT CAGCTCCTGT GGGGTCTTTT GGACCAGCTG     2150

ATGTCAGTAG GGTCCTTTAG AGCAGCTGGC ATCAGTGGGG TCCTTCAGAC     2200

CAGCTGAGTC ATTAGAATCA TCAGTATGCA GGACCTTAAG GAATATCTCA     2250

AAGAAAAAAA GTTTCATTAT GTTAAAATTG TTATCTATAG AGCAATTAAG     2300

GGCAACTATA ATCTAGTAAC AGGATCTACA TGATTCTGGG ATAATAGGCA     2350

CCAAACTACT ATGAGGAAGC AGGTCAGAGA GCAGCTGACT TCATGATTAA     2400

TGCTGAATGT TCTGCAAGCT TGGCGTATCT TCATTTATCT CCCTTCCCTC     2450

TTCCCTGATT AATTTTATAC AGTTCATAGG GGCAGTTTCA AAACCACCCA     2500

CCCAGAACAG AGGAGCCCAC AAATTCCACC AATCTGTCAC CCTTGGGGAG     2550

CCCAGAAGAG AATTATGAGG TGGAGAAATC CCATCAATAT GCCTCGTGTG     2600

TTTCACAGAG GTGAAGACCT TGGACTAGTG GAAATGGCCC TAGGTCAAAG     2650
```

```
AGACAAAACC CACGCCCTAA CAGGAATCAA GGTGAGGATC CTAAGTGTTA      2700

CGAGGGGGCT CTCCCCCTTG CAACACCAGC AGAGGGGGCC AAACAGAGCC      2750

CTCGCCATTG TTAGCACCGA GAGCCCCAAA ATAAGTATCT CTGAATCCCT      2800

TCATTCCACC TGTATAGTCT CGGGGAAGGA AGGGCCTTTG TCTGAAGAGG      2850

GTGACCCAGT TGTGCAGAGA GAGAGTCTTG GCTTTCACGG GAATCAAGGT      2900

GAGGACTCTG AGGGCGGATG AGAAGACCTC TCCCCAAAAA AGGCACATTC      2950

ACAGAGCCCT GCCGCTGCTG TCAGGCCTGT GAGGCCAGGA AGGGGTGGCC      3000

TGTTTGGCAC GCTTAGATTT CCACAGTGGG GGCTGAGGGA GGTGGGGGTA      3050

TTGTTTGGAG GCTGGCGGAT TTGGGTCAGC ACGCATATTC GTCCCAGGCT      3100

GCTAGATACT GAGGTGAGGA CCCTAGTGGA GACGAAGGGA CCAGCAACGC      3150

TAGAACAGTG ACGTCCGGTA GCGTCCAGCC GTCAGCCCCT CAGACGCCAC      3200

GGGCTGCCGG ATGTGAGTCA TCCTGACTTC CGCTTTGAAA AAAAAGACCC      3250

GAGCGGATGT GGCTCATCCT GACTTCCGCT TTGGAGGCGA GGACCCGAGC      3300

GAGTGTAGGG GGTGCGGCGT CTGGTCAGCC AGGGGTGAAT TCTCAGGACT      3350

GGTCGGCAGT CAAGGTGAGG ACCCTGAGTG TAAACTGAAG AGACCACCCC      3400

CACCTGTAAC AAAGAGGGCC CCACTAAGTC CCGCTTCTGC ATTTGGTCCT      3450

GAGAGGCTCC GGTAAAGCCG TCCGGCAATG TTCCACCTGG AAAGTTCCAG      3500

GGCAGGGGAA GGGTGGGGGG AGGGGCAGTC GCGGGGAAG GAGGTTTGGA       3550

CGCAGGGAAT AGGCCTCATT CTGCACGTAG GGTGGGTGTA GGCCCTAACT      3600

GAAATCAATT TGAGGGCCCT AAATGTGGAC TGAAGAGAAC ATCTCCTACC      3650

CTTAACAAAG GTGGCCTCAC TAAGTCTCGT CCCTGAAGAC GGCTCTGGGA      3700

GGCCCCAGCA AAGCTGTGCC TGGAAAGTCT CAGGGAGGGG AGGGCCTTGA      3750

ACCTAGGAAG CAGCCCTGCT TCTGCTCATA TGGCATCAAC CTAAAACCTA      3800

ACTGGGGTTA AGGTGAGGAC TCTGAGTATT AATGAGCGGA CCTCTACCCA      3850

AAAGAGGAGT CATGCTGGGC AGTTCCCAGG CCGAGGTGAC ACTGGGTTTT      3900

AGATGGTCCC AGGCTGACAT GACAAATGCA GAGCAACCTG ACTTCCTCTC      3950

CCGGGACTAA AGAAGTTGAG GGCTACATCC AAGACCCACA TCTGCTGCCA      4000

GCAATAGGAA GGTCAGGGCA AAGCTAGCAA GCTGAGATGC TCTCTAGTTT      4050

CCTCTGGAAG GTGGTCTCAG GGAGGTGAGG GTCTGGTGTA TGGGGTAGGT      4100

CTAATGCGAC AGAGAGGCCC AGTCTCTAAC AGGAAGCAAG GATGTGACAC      4150

TGAGTGATGA GGAGGGGACT CCAACCAGAA AGAAGTGCCA TATAGAGCCC      4200

ACTCTTGTTG TCAGACCAGG GAGACCTGAG CATGGCATGT TGAGTTGTAC      4250

TCACTCTCCC CAAGACATCT CAGAGAAGTG AACGACCCCA TTAAAGAGGG      4300

CAGCCTGGCC GGGCGCGGTG GCTCACGCCT GTAATCCCAG CACTTTGGGA      4350

GGCCGAGACA GGCGGATCAC GAGGTCAGGA GATCGAGACC ATCCTGGCTA      4400

ACACGGTGAA ACCCTGTCTC TACTAAAAAT ACCAAAAAAA AAATTAGCGG      4450

GGAGCGGTGG CGGGCGCCTG TAATCCCAGC TACTCGGGAG GCTGAGGCAG      4500

GAGAATGGTG TGAACCTGGG AGGCGGAGTT TGCAGTGAGC CGAGATAGAG      4550

CCACTGCAGT CCGGCCTAGG CGAAAGGGCG AGACTCCGTC TCTTAAAAAA      4600
```

| | |
|---|---|
| AAAAAAATAA AAAGGCAGCT TGAGGTCAGC AGAGGGAGGG TTTCCAGGTT | 4650 |
| GTGCCAGATG TTATGATAAG AACTCTGACG ACTGCAGGGG GCTCCCACCC | 4700 |
| CATATTAGTG GAGCCACACA TCCTCAGTAC TGTCAGCTCT GAGAGACCCC | 4750 |
| AGGCAGAAAT GTGAAACAGA GTGCCCATCA GTTCCCACTC AAGGGTAACA | 4800 |
| GGGAAATGAG AGTTTAATCT GAGGGTGTGA TCACTTGTCA ACAGAAGTAA | 4850 |
| TGTACTAATT GGTCCATTCT GGCATTACTA TAAATACCCA AGACTGGGTA | 4900 |
| ATTTACAAAG AAAAGAGGTT TAATTGGCTC ACAGTTCTGC AGGCTGTACA | 4950 |
| GGAAGCATGA TGCTGGCATT TGCTCAGCTT CTGGGAGCAG GGCTCAGGAA | 5000 |
| ATTTACAATC ATGGCAGAAG GGGAAGGGGA AGCAGACATG TTACATGGCC | 5050 |
| AGAGCAGGAT CAAGAGGCCA GGGGAGGCGC TACACACTTT TAAATGACCA | 5100 |
| GATCTCATGA GAAGTCATCG TTAAGGGGAA TGGTGCTAAA CCATTCATGA | 5150 |
| AAAACCTGCC CTCATGATCC AGTCATCTCC CACCAGGCTC CACCTCCAAC | 5200 |
| ATTGAGGATT ACAGTTAGAC ATGAGATTTG GTGAGGATAC AGATCCAAAC | 5250 |
| CATATCAGGG AAGAATCTTA GACCCTCTCA TGAGTCAAAT TTAGAGGCTG | 5300 |
| AGTTGGGACT GTATGTGGGA CCATCTATCA CAGGGCAGTT ATCTGCCTGC | 5350 |
| CACAGCTTTT ACTTTTGGGA AGACCACATT TGGTCAGATA AGGCCACCCT | 5400 |
| CACTTCCTCC TATGGGTTCT CAGGGATGTT CACTCTTACC ATGACGACAT | 5450 |
| AGGCCTCAGT TCAATAAAAA GGAGAGCTCC TCTACCAGGA GTCAAATTGA | 5500 |
| GGAATCTGAG AATTCAAGGA ACCACTGAAC CCTTAACAGT GGAGACATCA | 5550 |
| AAGAATCCAG TCCAACCCTT TATTTTCAGC CCTAGAAAGC TCAGGAAAGG | 5600 |
| GTTATCAGGT TTAGTGTCCC CCTCTCTTTT TTATATAAGA TCTAAGAGAG | 5650 |
| GTGAGATTCT TAGTCTGACG GTGTAGCCAC CACTCAGCAG AAGGGGGCTG | 5700 |
| GTGCCAAGCC CTACATGAAG CCAAGGTGGG GACCTTGAAT GAGAGCTGAA | 5750 |
| GACTCTAATG ATTCCAAGAC ATCAAAGACC CCACTGAACT CTCAGCACTG | 5800 |
| GGTGTCACTT CTCAGGGTGG TGGTTGAGGC ACCCCTTCAA TTTCTTCTCA | 5850 |
| TGAGTCCCAG GGTGCTTTGA GGTGTCAAAT TCACAGTAGC GGAAGGGAGT | 5900 |
| GGCTCAGGCC TGCAAGACTT CATATGATAA TCCTAAAAGT TAACTGATAA | 5950 |
| AACCCCAAAC ACCAGAAGAC AGGAGGCCGC ACTGCCAGTA CCTCCTGTCA | 6000 |
| CCATAGTAAG CCCAAGGAAG GGCTGACAGA ATGCAGTCTG AAACTCACTG | 6050 |
| TAGGGGTTCT GTGGTTCTTC TCTGGTGTCT CAGGGGAAAG GATAACCAGG | 6100 |
| ACGACAGGAG CCTTGTGGCT TTCTAGAACA GTGCCTTCAG GGAAACTTGC | 6150 |
| AAAGGCAGGC TTCCTTCAGT AAAGCTAAGA TGGGGTCTTC CAGCTGAAGG | 6200 |
| TGCTCACAGA TCTCATTCTC CCATCTCCAG GTATACTAAC CATCTATTCT | 6250 |
| TCTGCCCACA TTTCTTGGTT TACCCAGCCA TCATGCCTCG TGGTCAGAAG | 6300 |
| AGTAAGCTCC GTGCCCGTGA GAAACGCCGC AAGGCCCGAG ATGAGACCCG | 6350 |
| GGGTCTCAAT GTTCCTCAGG TCACTGAAGC AGAGGAAGAA GAGGCCCCCT | 6400 |
| GCTGTTCCTC TTCTGTTTCT GGGGGTGCTG CTTCAAGCTC TCCTGCTGCT | 6450 |
| GGCATTCCCC AGAAGCCTCA GAGAGCCCCA ACCACTGCCG CTGCTGCGGC | 6500 |
| TGCGGGTGTT TCATCCACAA AATCTAAAAA AGGTGCCAAG AGCCACCAAG | 6550 |
| GTGAGAAAAA TGCAAGTTCC TCCCAGGCCT CAACATCCAC TAAGAGCCCA | 6600 |

```
AGCGAAGATC CTCTAACCAG GAAGTCAGGG TCGTTGGTGC AGTTCCTGTT      6650

GTACAAGTAT AAAATAAAAA AGTCCGTTAC AAAGGGAGAA ATGCTGAAAA      6700

TTGTTGGCAA AAGGTTCAGG GAGCACTTCC CTGAGATCCT CAAGAAAGCC      6750

TCTGAGGGCC TCAGTGTTGT CTTTGGCCTT GAGCTGAATA AAGTCAACCC      6800

CAACGGCCAC ACTTACACCT TCATCGACAA GGTAGACCTC ACTGATGAGG      6850

AATCCCTGCT CAGTTCCTGG GACTTTCCCA GGAGAAAGCT TCTGATGCCT      6900

CTCCTGGGTG TGATCTTCTT AAATGGCAAC TCAGCTACTG AGGAAGAGAT      6950

CTGGGAATTC CTGAATATGT TGGGAGTCTA TGATGGAGAG GAGCACTCAG      7000

TCTTTGGGGA ACCCTGGAAG CTCATCACCA AGATCTGGT GCAGGAAAAA       7050

TATCTGGAGT ACAAGCAGGT GCCCAGCAGT GATCCCCCAC GCTTTCAATT      7100

CCTGTGGGGT CCGAGAGCCT ATGCTGAAAC AGCAAGATG AAAGTCCTGG       7150

AGTTTTTGGC CAAGGTAAAT GGTACCACGC CCCTGTGCCT TCCCAACCCA      7200

TTACGAAGAA GCTTTGAAAG ATGAAGAGAA AGCCGGAGTC TGAGCCAGAG      7250

TTGTAGCCAG GCCTTGCACT ACTGCCATAG CCAATCAATC TCCCAAAGCC      7300

AAGTTTACCT GCTGTTCTCA CCCCCAATGA GGTCTTAGGC AGATTCTTTA      7350

CTTTGTAATT CAAAAGGCCT GTTAACCTTT GTTCTTGTTA TGCATGAATA      7400

ACTTGTTGAC TTTTTTTTTT TCTCTTTTTC AACTAGTGTT TCAACAGGTT      7450

TATTTAGATT CAGAATGTAA ATTTACAAAT GATATAGATC ACCCTGTTAT      7500

TGCTGTTTTT CAGGGACAGT AGAAAGTGTT TTGTTTTTTG AGTGAAACAA      7550

CTTATTAATA AAAATCCTTA AATCACTTTT GTAATCCAGG ACAAGAAAAT      7600

GTGGCATTAG AGTAGAAATA TCTTTGGAAA TGTGAAAGAC CCCATAGTGA      7650

AATATTTGGG ATCAGAAGCC AGAGGTGTAA AAGTGGTCAA TTCTTGGTTT      7700

ACTTCATTTA ATCTTTCTTT TCATAAAGAT ACATACCTGG ATTTGTTTAT      7750

GTTATTCAAG AATGTGTGAG AAATTAAACC ATAGTTAGTT AATCCTCTTG      7800

TTTATGGCTC TTACTTTAAA TATTTTAATT GAGCATCTGT TCTTTGGGAG      7850

TCTTCCTGCT TGTACTGGGA ATGTTTAGTC AAAGAAGACC AAGCTTGTGC      7900

TCATGCAATT GTAGATTCTA GGAGAAGCTG TCATCATGGA AGGTGAGACA      7950

CTTCATAAAA AATAAAAGAT AGGAAAAAGA AGTGATGAAA GCAATAGTTT      8000

TCATTGCTAA GCAGCATTTT GGCTGAATGG GGTTTTTCAG TCTTAGAATG      8050

TTGCGTATTC TCAGCCGGGT GCAGTTGCTC ACATCTGTAA CTCCCAGCAC      8100

TTTGGGAGGC TGAGGTGGGT GGATCACCTG AGGTCGGGAG TTCGAGACCA      8150

GCCTGACCAA CATGGAGAAA CCCTGTCTCT ACTAAAAATA CAAAATTAGC      8200

CAGGCGTGGT GGCGCATGGC TGTAATGCCA GCTACTCGGG AGGCTAAGGC      8250

AGGAGAATCA CTTGAACCCA GGAGGCGGAG GTTGCTGTGA GCCGAGACTG      8300

CGCCATTGCA CTCCAGCCTG GGCAACAAGA GCGAAACTCC CTCTAAAAAA      8350

AAAAAAAAAA AAAAAAAAAA AAATTGTTGC ATATTCTCTG AGATATCCTG      8400

GATTTTTTTT TTTAATCTC AACTGGAATG AAGGTAATGT CTCTGATCAA       8450

AATGATAGTG GTAATTGCCA CTTCCTGATG TCTCAGTTGA CGAGACAGGC      8500

ACATTTGCAT GCATTACATA TATTCCACCA GTACTACGAG ATGGGGCTTA      8550
```

-continued

| | |
|---|---|
| TCAAACCCAC TTTACGGTAA AGAGTCTGAG GCTCACTGAG TTTGGTAATT | 8600 |
| TGCCAAAGTT TACAGGGCCA GTAGTGAAAG GGTTGGGATA AGCCTCCTGA | 8650 |
| TCTGAATTAC CCTAGAGCCT ACCCTGTTCC ACCCCTCTCA GCCTGAGGCA | 8700 |
| AACCTTGAAA AAATATTTCC GTTTTCTTCT CATTACTGCG GAATGTGTTT | 8750 |
| CAGGTGATAA AAAGAATAAC CTTGTAACCC AAACTAGTAG ATTGGAATAC | 8800 |
| ATAGCCACAG CAACAATAAT ACCAAAAAAA CTGAGAGGTA TAAATAAGTA | 8850 |
| AAAGAGGCAA TATTCAGTGA CAGTATGATT ATCTACATTC GCAATGTTAG | 8900 |
| ATAACCTCAA AAGATCAGGG GCTCCCAAAT CATCCTGAAC AATCTCTTCC | 8950 |
| CTGTAGAAAA TAAATCTATC AGAACAGAAA TTACATGAGA ATGTAAGGCT | 9000 |
| GGCTGATAGA AGAAATAGAT CAATGTATCT TATCTCTGGC TGCCCATCTC | 9050 |
| CAATCCTAGG CCCCCTGCTT TGTGCTACAG CTTTGCGGTA TCACACCACT | 9100 |
| CCTAGGACAG AGACCCATTC TCTGCAATGT TTACAGAGAG GAAATTGTTC | 9150 |
| TAGAATTTGC AGAGATGTGG CATTTTGCAG GAAGCATTTA ATCCAGAGAC | 9200 |
| AGAGCCAGAT GAGGGCTGGG AGACCACATC CCAGAATATC AGGCAGGGGT | 9250 |
| TTACATAGAC CATTCCCTTC TGCTCTCAGA CACGGTCCTA GGCTGAGCTG | 9300 |
| TCAGTCTGAG CATCCCCTCA CATATTCTTC AGGTGTCTGA GAGACATAAG | 9350 |
| AGCCCTAAGG GCAGCATCCT CAAGTCAGTA GGGAAAGGAA TCCCAGCCTC | 9400 |
| TTATAGGAAT GAAGGTAATA AACCTAAATG AGGGTGATGG AAGGACCCAG | 9450 |
| CCAGAACAGT TGGGGGCCTG TAAAGTCACG TTCCAATTGT AGTCTTGTGA | 9500 |
| GTCCAGAACC GTCCTGGTGG ACACTGACTT CCAATTCAGG TCCCAGCAAG | 9550 |
| GTGAGGACTT TGGTCTGAAG GCTATGGCCT CAGGTCAGTA GGGAGTGGAG | 9600 |
| TCCCAGGAAG GGGGCAGAGT CAAGGTGAAG GCCTGGCATG TGGATATGGG | 9650 |
| GACCACTCAA CCCATAACTG GCTGGCGTGC CTCTAGTCAT TCCTTTGCTA | 9700 |
| TTAGCCCTAG GAGGCCTAGG GAGGAGCTGG CAGGCCCAGG TGCCCGTGTC | 9750 |
| TTCTTCCTGG AGAATCTCAA GGAGATGAGA GACTTGATTT ACAGGCTGGC | 9800 |
| CTCCCAGTTA AGCAAAGAGT GGAATCCCAG ACCATGATAG GTATTAAGGT | 9850 |
| AAAAATCTCA TATGAGGAAA GAGGCAAACA ACTGCTAGAG AGGTGAACAG | 9900 |
| AACAAGGACG TCCTTAGAAA GTTATGCCGG GCCAGACGCG GTGGCTCATG | 9950 |
| CCTGTAATCC AGCACTTTGG CAGGCCGAGG TGGGCGGATC ATTTGAGGTC | 10000 |
| AGGAGTTCAA GATCAGCCTG GCCAGCATGG CAAAAACCCG TCTCTACTTA | 10050 |
| AAAAATACAA AAATTAGCTG GGCGTGATGG TGGGCGCCTG TAATCCCAGC | 10100 |
| TACTTGGGAG GCTGAGGCAG GGAGAATTGC TTGAACCTGG GAGGCGAAGC | 10150 |
| TTGCAGTGAG CTGAGATCAC GCCACTGCAC TCCAGCCTGG GCAACAGAGC | 10200 |
| GAGACTTTAT CTTAAAAAAA AAAAAAGAAA AGAAAGAAA GTTATGCCCT | 10250 |
| GGGAGGCCAT AAGCATAGCT TTCAGGCTGA GGTTACCCCA CATTCGCTGA | 10300 |
| GGGGAGGGGA GTGGTCTCAG GGACAGGAAG TCCTTGGACT AATAGGAGAG | 10350 |
| GCCCCATTCA GTAGAGGGAG GAGATTGGCT CCTTAACAGG ATTCAACATG | 10400 |
| ATGCACTGA GTGACAATGA GGGGACCCCT CTCAGAAAGA AGAGGGTCAC | 10450 |
| ATAGAACCTT GTCCCTATTG TCAGACCTGA GACCTGGACA TGATGACATG | 10500 |
| ATGTATCATA CTCACTTCTT CCCAGGTAAT CTCGCGGAGG TGAAAAATAT | 10550 |

-continued

| | |
|---|---|
| TAACAAAGTG GGCAGCCTCA GGTCAGTAGA GAGAAGATTT CTAGGTTGTT | 10600 |
| GCAGAAGTAA ATGTGAGGAC CCTGAAGACT GAGGTGAACA CCTACCCCAT | 10650 |
| AACAGTGAGG GTAACACAGA TTCCTTCCAC TACTGTTAGC CTAGGGAGAA | 10700 |
| CATGAGCAGT TATGGCAATA TGAAGCAAAT TTTACTTCTT CTTAGGGTGT | 10750 |
| ACCAGGAAAT TGGTCTTCAA TTCCCTTCAT ATGGGGAGAC AGGCCTCAAG | 10800 |
| TCAAGACAGG GAGGATTTGC ACAGGGTGTG ACAGGAATAA GGATGAGGAA | 10850 |
| ACTGAAGAGT ATGGGACCAC AGACCCCACA TCAGTAGGAG CCACACAGAA | 10900 |
| TCCTCCCTAC TGTCAGCCCT CAGAGACCCC AAGCAGAAAT GTCAGGTGGA | 10950 |
| GTTTCCCATC AGGTCCTACT CAAGGGTAAC AAGGGAAGTG AGGGTCTTGA | 11000 |
| TCTTAGGGTG GTAGTCTCAC ATCAACAGAA AAAGAAATCT TAGACCTGTC | 11050 |
| CAGAAGTTAA AAATTTAGGA CCCTGAGTTG GGACCCTGCA TGGAACTACC | 11100 |
| CATGATAGGG CCTTGAACTG CCTGCCACAG GTTTCATTCT TGTGAGACCA | 11150 |
| TTGGCAGGTA TATAGCCAGA TGAGGCCATC CTTGCTTCCT CTTGCTGGAT | 11200 |
| CTTAAGAAGG TGTGGGCCTC ACTTTGAGGA GATGTCATCA GGTCAAGAAG | 11250 |
| GAGGGGATCC CCAGGCCCTT CCAGGAGTAA AATCAGGGAA TCTGAGTGGA | 11300 |
| GACTGATGGT ACAACATAGC CTTGAATAGA GGGGACAACA AAGTGTCATG | 11350 |
| CCCTACCCTT TGATATCAGC CTTAGAAGAC TCAGAGCAGG GCTGTCAGGG | 11400 |
| GAGGCACCTC ATCACTTCTT TATATACGGT CTAGGGGAGG GGAAATCTTT | 11450 |
| GGTCTGAAAG TTCAGCTACC AGTCAGCAGA AGAGATCCAA TACATGCCAG | 11500 |
| TCACTGTGCC AAGTGCTTTC CATACATTAC CCACATCCTG CCAGTTCTGC | 11550 |
| CAGACAGGGC TTACCAAACC CATTCCATAG ATGCAGAACC TAAGGCTCAT | 11600 |
| AGGATTTAGT AATGTGCCCA AGTCACACTG CTAGTAATGA CAGGGCTGGG | 11650 |
| ATGAGAACAC TGGTCTGAGT TAGTCAAAAG CCCACACTGT GCCACTCCTC | 11700 |
| TCAGACAAAG GATGACCTTG TTCCTTAATT AACTTTTCCT CTCGTTACTG | 11750 |
| CAAAATGTAC CAGAGGCAAT AAAAAGAAAG ACTGTGGCCA AACGATGGAC | 11800 |
| TGTAATATAT AGCCAGAACA ATAAAAATAT CAAAATAAAT GGAAGGTTTG | 11850 |
| AGTAAGGAAA AAAATAATAT TTTGATGACA TAATTTACAT ACATATGTGA | 11900 |
| TGTCCAATAA ATTCAAAAAA TGAGGAGGTA CAAAAAAATC ATCTGAGCCA | 11950 |
| CTTCCTTAGA AAAGTAAAT ATATCACAAC AGAAGTTACA TGAGACCCTA | 12000 |
| AATCTGGCTG GGCAAAAATA GGAGATGGAC ATTTGCTTTT TCTCTTATAG | 12050 |
| CCTACCACCT ATCCTGGCCC CCTGCCTTGT GCTGTAGATT TCCCATATTG | 12100 |
| CATCACTCCT AGGGCAGGGG CCTGTTCTCT GAAAGGTTTG CAGAGAGGAC | 12150 |
| ACTGCTCAAG AGTTTCGCAG AGATGTGGCA TTTCCCAGGA AGCCTTTAAT | 12200 |
| CCCACTGCAA GAGCCTGTAT GAGGACATAC ATAAATCAGG ACTGGAAAAA | 12250 |
| CAAACACTGC AGAATATTGG TTATTACCAA AAGACTATCC CCTGCCTGCT | 12300 |
| TTCAGACCTA GAGGGTCCCA GGCAGAACTG TCAGGATGAG CATCCTCTCA | 12350 |
| TTTATTTTTC ACAGTTGTCA GGAACTTGAG AGCTTTAGCC TAAGGAGGGC | 12400 |
| AAGCTTAGGT CAGGAGAGAG ATAAGACCCA AGATCTGTTA GATACAAATG | 12450 |
| CCAGATCCCT TAAAAGTAAT TAAGAAAGCA CCCATCCAGA ACACCGGGGT | 12500 |

| | |
|---|---|
| CCCGAAGAGT TCAGGCCCTG CTGTTGACCC TTGGAGGTCC TGAATTCAAT | 12550 |
| GGTTGGATGA AATATAGAGA GGCCTTGAAA GATGAAGCAG AGAGAGCCTG | 12600 |
| AGCCAGAGCT GCAGCCAGGG CTGTGCTACT GCCATGGCCA TGGCACATAC | 12650 |
| CAGAGCCACG TCCAGCTGCT CCTCCTACAT CTAGTGAGAT CTGAGACAGA | 12700 |
| TTCTTCACTT TGTAGTTGAA AAGATAAGTC AACATTCTAA GTAGTGGAGA | 12750 |
| GTCAATTTTG ACCTAGGGCA AACATATTGT ATGTCTTATT TTTGTTTTTG | 12800 |
| CTCTACTTGA ATAATTGGAA GATGTATCTT TTTTATTTTT GGTACTTTTA | 12850 |
| AAATGTATTC ATTTTAATAG AAGATTTATT TAGCTTCAGT ATCTGTGTTT | 12900 |
| ATGAATAACA TGGATAACAT ATTTATTTCT GTTTTCCATA TATAAATGTA | 12950 |
| AAAGTGCTGG TATTTTTTTA TCAACAAACT GAAAATCCTT AGGTCTCTCT | 13000 |
| TTGTGGTCCA GAACAAGATA ACATAGCATA TGAATAAGGA CTTTTTTATT | 13050 |
| GTATAAATTT AAGTTGTACA GTAGGACGTT TTGATATACA TATATGGCCA | 13100 |
| TGCACCACAT GATGATGTCT CAATCAGGAC CACATATACA ATGGCAGTCT | 13150 |
| CGTAAGATTA TAATGGAGCT AAAAAACTGT ATTGTTTACA TGTGTGTGGT | 13200 |
| GATGCTGGTG AAAACAAACC TACTGCACTA TCAGGCCTAT AAAAGTATAG | 13250 |
| CACATACAAT TATGTGCAGT ACATAGCGCT TGATACTGAT AATAAACAAC | 13300 |
| AATGTTACTG GTTATATCT TTATTATACT ATAGTTTTTT TTAAATCAGG | 13350 |
| TTGGTGCAAA AGTAATTACA TTTTTTGCCA TTAAAAGTAA TAAGAATTGA | 13400 |
| GATGGGTAG TAGTAGTAAT AATATTCTAG TAATACTAAA TAAGTAGTAA | 13450 |
| TATTAATAGG TAGTACTATT AAAATATTAA TATTAATTAA TAAGTAGTAA | 13500 |
| TATTAAAAGT AGTAATAATT GGGACGGAGT CTTCCTCTGT TGTCCAGGCT | 13550 |
| GGGGTGCAGT GGTGCAATCT CAGCTCATTG CAACCTCTGC CTCCTGGATT | 13600 |
| CAAGCATTCT CCTACCTCAG CCACCTGAGT AGCTGGGATT ACAGGGGCCT | 13650 |
| GCCACCACGA CCAGATAATT TTTGGACTTT TAGTAGAGAT GGAATTTCAC | 13700 |
| CATGTTGGTC AAGCTGGTCT TGAACTCCTG ACCTCAAGTT ATCCACCCGC | 13750 |
| CTCATCCTCC CAAAGTGCTG GGATTACAGG TGGTACTTTT ATTATTATTT | 13800 |
| TAGAGTGCAC TCCTTCTACT AAAAAAAAAA ATGTTAACTG TAAAAACAGT | 13850 |
| CTCAGGCAGG TCCTTCAGGT TGTATTCCAG AAGAAGGTGG TGTTATCATA | 13900 |
| AGAGATGACA GCTCCATGCG TATTATTGTC CCTGAAGACC TTCCAGTGGG | 13950 |
| ACAAGATGTG GAGGTAGAAG ACAGTGATAT TGATGATCCT GACCTTGTGT | 14000 |
| AGGCCTAGGC TAATGTGGGT GCTTTTGTCT TCATTTTTAA CAAAAACGTT | 14050 |
| TAAAAATTTA AAAAGTAAAA ATAGAAAAAA GCTTATAAAA TAAGAATATA | 14100 |
| AGAAAGAAA ATATTTTTGT ACAGCTGTAC AATGTGCTTA TGTTTTAAGC | 14150 |
| TAAGTGTTAC TACAAAAGAG TCAAAAAGCT AAAAAAAATT AAGAAGTTTA | 14200 |
| TAAAGCAAAA AAAGTTACAG TAAGCTAAGG TTAATTTATT GTTAAAGAAA | 14250 |
| GAAAACTATG CTTGAGAATT TAGTGTAGTC TAACTGTACA ATGTTTATTA | 14300 |
| AGTCTATAAT AGTGTACAGT AATGTCCCAG GCCCTCACAT TCACTCACTA | 14350 |
| TTCAATCACT GGCTCACCCA AAGCAACTTC CAGTTCTGCA AGCTACATTA | 14400 |
| ATGGTAAATA CTCCACACAG GTGTATGATT TTAACAATC TTTTGTACCA | 14450 |
| TATTTTTTAC TGTACCTTTT CTGTGTTTAG GTACACAAAT ACTTAGCACC | 14500 |

| | |
|---|---|
| GTGTTACATT TGCCTATAGT TTTCAGTGCA GTCACATGCT GCACAGGTTT | 14550 |
| GTGGCCTAGG AGCAATAGGC TACACCAAAT AGCCTACGTG TGTAGTAGGC | 14600 |
| TATATACCAC CTAGGTTTAT GTAAGTATAC TCTATTATAT TTGCACAACA | 14650 |
| ATGAAATTGC CTAACAACGC GTTTCTCAGA AAGTATCTTC ATTGTTAAGC | 14700 |
| AATGCATTAC AGTACATGGT GAAATGCTTA CTACAGGTAA GCAATTTAAT | 14750 |
| ATATCCATTA TATCATATAG TTACCTTGTT TTGTGGTAAG AGCAGCTAAA | 14800 |
| ATCTACTCTT AGAAAATTTG CAGTATGCAA TACAATATTA CTAACTGTAG | 14850 |
| TCCTCATACT GTACTTTAGA TCTCTAGATT TATTCGTCTT ATAAAACTGC | 14900 |
| AACTTTGTAC TGTTTGACAT GCATCTCTGC ATCCCCTCCC CACCCTGCCT | 14950 |
| CTGGTAACTA CTGTTTTATT CTCTTTTTCT ATGTATTTAA CATTTTTTTC | 15000 |
| TTTTTCGATT TTACATATAA GGGATATTAA TAGCATGCAG CATTTTTCTT | 15050 |
| TCTGTGTCTG GTTTATTTCA TTCAGCATAA CGTCCCCCAA GTTCATCTGT | 15100 |
| GTTGTTGCAA TGGCAGAATC TCTTTCTTTT TCAAGGCTAA ATAACATTTT | 15150 |
| TTTAAATTTT ATCTTAGTTT CAGGGGTACA TGTGCAGGTT GTTATATAGG | 15200 |
| CAATTGCATG TCATGGGGGT CTGGCGTACA GATTATTTCA TCACCCAGGT | 15250 |
| AATAAGCATA GTACACAATA GGCAGTTTTT CCATCCTCAC CCTACTCCCA | 15300 |
| CCTTCCGCCC TTAAGTAGGC CCCAGTGTCT GTTGTTCCCT TCTTTGTGTC | 15350 |
| CATGTGTACT CAATGTTTAA CTCCCACAAA GAACATGCAG TATTTGGTTT | 15400 |
| TCTGTTTCAT TGTACATATA TACCACAATT CCTTTATCCA TTCATCCATT | 15450 |
| GGTAAACAAT TTTGTTGTTG CCGCATCTTG GTCATTGAGA ATAATACTGC | 15500 |
| AGTGAACATG GGGGCATAAA TATCTACAGG AGGTGATGAT TTCGTTTCCT | 15550 |
| TATGCCCAGA CAAGGGATTG CTGGGTCATA TGGTAGTCCA TTTTCAATTT | 15600 |
| TTTGAGAAAG CTCATACTGT ATTCTAGAAT GGCTGTACCA ATTTGCATTT | 15650 |
| CCACCAATAG TGTAGAAGCG TTCCATTTTC TCTACACTCT TGCCAACATT | 15700 |
| CATCTCCAGT GGGTTTTTGT TTGGTTGTTT TTGTTTTATT TTTTTATAAT | 15750 |
| AGCCTTCCTA ACTTGTGTGA GGTGATATCT CGCTGTGGTT TTGATTTGCA | 15800 |
| TTTCCCTGAT GGTTAGTGAT GTTGAGCACA TCTTTGTATA GCTATTGGAC | 15850 |
| ATTTTTATGT CTTCTTTGAG AAATGTCATA CAAGTAGTGA ATTTTCTTGA | 15900 |
| GTACTGATTA TGTTGGAAAT GTGATTGAAT ACTGTATTAA AAATTGTTGA | 15950 |
| GATCAAAAAA TTTTTTTAAA AAAGGTTGTC TATTCTTGGT TTGCCTAATT | 16000 |
| CCTTTTAGTC TTTCTTCTTA TAAAATTAAG AGTTACATAT CTGGATTTGC | 16050 |
| TTAGATTATT AAAGAATGTA GGAGAGATTA ATCCTAATT TATTGGACTT | 16100 |
| CATACTCACT CTCTTGTTTA TTCCTTAATC ATTAATTGAG CATCAGCTCT | 16150 |
| TTGGAAGTCT TCATGTTAGT ACTGGGAATG TTTTCCCCAA AACAAATCAA | 16200 |
| TTTCTTGCCC ATTTAATTTT AGAGTCTGGG AGCAGCTGTC ATAAAAAAAA | 16250 |
| AAAAGATGAT GAGGTGCTCT CTAAAACTTA AGAACAAGT ACAAGGAGG | 16300 |
| AATGAGAAAA AGAGGAGGTT TGAGATGAGA GCAATCAAGT GTAAATGCCC | 16350 |
| TGAGGCAAGG CAGTTTGGAG TGTTAGGAAA CCTCAAGTCC CCCATTGGGA | 16400 |
| GGTAATTTTA AGGGAAACTA CATGGTGGGC TGGATGAGAC TGTGGGAGGG | 16450 |

```
GCCAGGCCCT CAGATGGTGC CTCTCAGAGG TGTGAGACAA AGCCTGGAAT           16500

GGGAAGTAGT TCTTAACAGT TATTTTGTGC TCACGGATAA ACCAGAGAGA           16550

ATCTGCACCT GGGGCAGGAA TGGAATGTGC CCTGTGCTCT TGTCCCAGTG           16600

CAGCAGAACA TAGTCACAGT GCACAAACTA GGTGCTTTAT ACAGTTGGTG           16650

CATTCAGTGT TGAGAGACTA AGCCCGGAAT GGGAAACTAT CCCTAACATT           16700

ATCACTTTCC TGTTGTTGGA AAACCAGAGA GAACCCCTAC CTAGGACAAA           16750

AGTGAAAAGT GTTCTATGTC CCTATCCTAG CACAGTCTAA TACAGTGCAC           16800

AACCTAGGTG TTCTATGTAC ATCATCTCTA GTGAGTTTCT GAGAAATAAG           16850

GGAGATGACA GCTTCAGGGG AGGTAAGATG CCCAGAAGCC ACCGTGCTGG           16900

CACTCTTTGT CCTGGGTTGG AGAATCAAGA GCCCGCTCTA TTAAAAGGAC           16950

TTTCAACAGG GGTGCAGCCA GGCATGGTGG TTCATGCCTG TAATCCCAGC           17000

ACTTTGGGAG GCGAGGCAGG TGGATCTCTT GAGATCAGGA GTTCAAGATT           17050

AGTCTGGCCA ACGTGGTGAA ACCCCGTCTC TACCAAAAAT ACAAAAATTA           17100

GTTGGGCGTG GTGGTGGACA TCTGTAATCC CAGCTACTAG GGAGGCTGAG           17150

GCACGAGAAT CACTTGAGCC CTGAGGCACA GGTTGCAATG AGAAGAGATA           17200

GTGCCTCTGC ACTCCAGCCT GGGTGACAGA GTGAGACTCC ATCTCAAAAA           17250

AAATAAATAA ATAAATAATA AAAATCAAAA CAGGAGTGGT TAACATAGAA           17300

GGGTGCCTAG GAGTTAGAAA AAAATATTGG TCATTGACAA AAATTTTGAG           17350

ACTTGAGTTG TATCCAATTG GAGAAGGCTC TTCCACAAAC ACTTTATAAA           17400

TTATATAATT TTCCTTGCTA AGCAGCATTT TGTTTGATTA TAATTTCTTT           17450

GTTTGGAGTT TGGTAATATG CTCAAGTTCA CAGGGTGAGA AGTGACAGGG           17500

CTGGGACTAG ACTCCTGTTG TGAATTCTTC TAGAGCCCAC ACTCTTCATT           17550

CTGTTCCTCT CTGCCTGGAG CAGACTTTGT GTTCTTTAAT TCACTTTTCT           17600

TCTCAATACT TCCAAATATA TCTCAGGGGT TAAAAGAAG GATTCTGTGC            17650

CCAAAGAATT GGATTGGAAT ACATAGCCAA AGCAATAAAG AATATCAAAA           17700

TAAATGAAAG CTACAAATAA AGAGGAGAAA GAGATATTAT TCAGTGACAA           17750

TATGATCATC TACATATGCA CAAGTCAGAT AACCTCAAAA TCAGGGACCA           17800

CACAATCATC TTGAACAGCT CCTTCCCCTT AAGAAGTAAA TCAATTAAAA           17850

GAGAAGTCAC ATAAGAGGCT AGTGCTGGCT ATTAAAAGAG TAAATCAGCA           17900

TCATTTTTCT CTGACAACCC ACCAGCTACC TTGGACTCCC TGCTTTGTGT           17950

TATAATTTCT TTACCTCACA TTAGCCCTGG GGCACAGACT TGCAAGGTTT           18000

GCAGTAGGAA CGCTGCCCAA GAGTTTGCAG GGATGTGGCA TTTCCCAGGA           18050

AGCCTTTATT CAGAGAGGCA AGAGAAAATA AGGAGGACAC CCATAAATAA           18100

ATACTGGAAA GACAACCACA CCAAAAGATA ACGGGGCAAT CTACCCAAAC           18150

CTCTTCTCAG CCTAGAATGC CCCAGGCAGT GCAGTCAGAC TGAGCATCCT           18200

CTCTTTTACC CTTCAGAGTT CTCAGTGAAG TGAGAGTTTT GACCTAAGGT           18250

GACCTCAGTT AACTAGAGGG AGGATCCAGG GTCTGGCAGA TATCAGGGAG           18300

ACCTTGAATG AAGAACAGGA GGAGCCAGAA CAGTGATGTC CATAGAAACC           18350

CGACTCCGCT GTCTGCCCTC ACAGGACCCA AACATCCCTG GCCTAATGTG           18400

GCTCATCAAA ACTTCAGCCT AGATCTCGGA GGACCTTGAT CTGAGCAGGA           18450
```

| | |
|---|---|
| TTCATGGCAT GGAATGTGGA GTCCAGGACT GGCCAGCAGC GAAGTGAGGT | 18500 |
| TCTTGAGTGA GTAAAAAGGG AAAACTAAAC CCACAAATAA GGGGACTTCT | 18550 |
| CGGAGCCCAA TCCATATTTT TAACCCTGGA AAGCCCTAGG CAGAGCTATA | 18600 |
| AAACTGGCTT GCTCTCATTT CAGCCTGGCG ATCTCAGGGA GGGGAAGGCT | 18650 |
| TTGTCTAACA GGGCAGCCTC AGTTCTTCAG AGGTCTCTTG GCCCTAACTA | 18700 |
| GAGTCAAGAT GAAGACCAAG CCGGTGCGCA TCTCAGGCCT GTAATCCCAG | 18750 |
| CACACTGGGA GGCCGAGGCG AGTGAACTGT TTGGGCCCCC CAGGAGTTCG | 18800 |
| AAACCAGCCG GGACAACATG GCGAAAACCT GTCTCTACAA AAAAAAAAA | 18850 |
| ATGGCGGGCA GCAGTGGAGC ACCCTGTAGT CCAGCTACCA GGAGGCTGAG | 18900 |
| GTGGGAGGAT CGCTTAAGCC CTAGGGTCA AGGCTGCAGT GAGCCAAGGT | 18950 |
| CACGCCACTG CGCTCCAGCC TGGGTGACAG AGAGAAACAC TGTCTCAAAT | 19000 |
| TAGCCGGGCG TGGTGCGGCG CACGTGTAGT CCCAGCTATT CGGGAGGCGG | 19050 |
| AGGCAGGAGA ATCGCTTGAA CCCGGGAGGC AGAGGTTGCA GTGAGCCAAG | 19100 |
| ATAGCGCCAC TGCACTCCCG CCTGGGTGAC AGAGCGAGAC TCCATCTCAA | 19150 |
| AATAAATAAA TAAATAAATA TAAACTTTTT TTTTTTAATT TTAAGGCAGG | 19200 |
| GCTCTGGCTC ACGCTTGTAA TCCCAACATT TGGGAGGAC GAAGCCAGCC | 19250 |
| TCATCGCTTA AGCACAGGAG TTCGAGGACT GGGAGGTGGA GGTTGTGGTA | 19300 |
| AGTCAAGATT GCGCGGCTAC ACTCCAGCCT GGAAGACAGA GAGAGCCCCT | 19350 |
| GTCACAAAAA AAAAAAAAAA AAAAAAAAAA AAGAAAGAAA GAAAGAAAGA | 19400 |
| AATATGAGGC CCACCGGTGC TAACCAGGGA ACCTCTCTCC AAAAGAAGGG | 19450 |
| CCCACCAAAA GCCCTAACCC TGTTTCAGGT CTTTGAAGCC CCAGGACATG | 19500 |
| GTCCGATAAC ATGCCTAGAC TTCCCCTCTA GGGACTATGG GAGGGGAGGA | 19550 |
| TTTTGGAGGT TGGCGGACTT CGCTCAGTAG AGGTGTTACT CTGCTCCGCT | 19600 |
| TAGTATCAAG GTGAGAACCC TGAATAAGGA CCTAGGGACC ACTGACTCCA | 19650 |
| GAACAGTGGG GTCCCAGCGT GTCACCCGCT GCTGTCAGCC CTCGGAGACC | 19700 |
| CCGAGCGGGG TGTGGCTCAG CCTCACTTCC GCTTTGAAAG TGAGGCAGTT | 19750 |
| GGCTGACGGG TGCAATAGCT TCAGTCAGGT TCGTGGCCTA GCGTGAGTCT | 19800 |
| TAGAACTGAT CCGGAGTAAA GGTAAGAACC CTCAGCGGGG ACTGAAGGGA | 19850 |
| CAATCCATGT TTTTAACCCT GGAAAGCCCT AGGCAGAGCT ATAAAACTGG | 19900 |
| CTTGCCTCTC ATTTCAGCTG GCGGGTCTCA GGGAGGGGAA GGCTTTCTCT | 19950 |
| AACAGGGCAG CCTCAGTTCT TCAGAGGTCT CTTGGCCCTA ACTAGAGTCA | 20000 |
| AGATGAAGAC CAAGCCGGTA CGGCGTCTCA GGCCTGTAAT CCCAGCACAC | 20050 |
| TGGGAGGCCG AGGCGAGTGA ACTGTTTGGG CCCCCCAGG AGTTCGAAAC | 20100 |
| CAGCCGGGAC AACATGGCGA AAACCTGTCT CTACAAAAAA AAAAAAAAAA | 20150 |
| TGGCGGGCA GCAGTGGAGC ACCCCTGTAG TCCCAGCTAC CAGGAGGCT | 20200 |
| GAGGTGGGAG GATCGCTTAA GCCCTAGGGG TCAAGGCTGC AGTGAGCCAA | 20250 |
| GGTCACGCCA CTGCGCTCCA GCCTGGGTGA CAGAGAGAAA CACTGTCTCA | 20300 |
| AATTAGCCGG GCGTGGTGCG CGCACGTGT AGTCCCAGCT ATTCGGGAGG | 20350 |
| CGGAGGCAGG AGAATCGCTT GAACCCGGGA GGCAGAGGTT GCAGTGAGCC | 20400 |

| | |
|---|---|
| AAGATTGCGC CACTGCACTC CCGCCTGGGT GACAGAGCGA GACTCCATCT | 20450 |
| CAAAATAAGT AAATAAATAA ATAAATATAA ACTTTTTTTA TTTTTTATTT | 20500 |
| TAAGGCAGGG CTGTGGCTCA CGCTTGTAAT CCCAACATTT TGGGCGGAGG | 20550 |
| AAGCCAGCCT CATCGCTTAA GCACAGGAGT TCGCGGACTG GGAGGTGAGC | 20600 |
| TGCCCCTGTA GTCCCAGCTA CCCAGGAGGC TGAGGTGGGA GGATCGCTTA | 20650 |
| AGCCCTAGGA GTCAAGGCTG CAGTGAGCCA AGGTCACGCC ACTGCGCTCC | 20700 |
| AGCCTGGGCG ACAGAGAGAG ACACTGTCTC AAATTAGCCG GGCGTGGTGG | 20750 |
| GGCACAGGTG TAGTCCCAGC TATTCGGGAG GTGGAGGCAG GAGAATCCCT | 20800 |
| TGAACCCGGG AGGCAGAGGT TGCAGTGAGC CAAGATCGCG CCACTGCACT | 20850 |
| CCCGCCTGGG TGACAGAGCG AGACTCCATC TCAAAATAAA TAAATAAATA | 20900 |
| AATAAATAGA TATAAACTTT TTTTTTTTTT TAATTTTAAG GCAGGGCTCT | 20950 |
| GGCTCACGCT TGTAATCCCA ACATTTTGGG AGGACGAAGC CAGCCTCATC | 21000 |
| GCTTAAGCAC AGGAGTTCGA GGACTGGGAG GTGGAGGTTG TGGTAAGTCA | 21050 |
| AGATTGCGCG GCTACACTCC AGCCTGGAAG ACAGAGAGAG CCCCTGTCAC | 21100 |
| AAAAAAAAAA AAAAAAAAAA AAAGAAAGA AGAAAGAAA TATGAGGCCC | 21150 |
| ACCGGTGCTA ACCAGGGAAC CTCTCTCCAA AAGAAGGGCC CACCAAAAGC | 21200 |
| CCTAACCCTG TTTCAGGTCT TTGAAGCCCC AGGACATGGT CCGATAACAT | 21250 |
| GCCTAGACTT CCCCTCTAGG GACTATGGGA GGGGAGGATT TTGGAGGTTG | 21300 |
| GCGGACTTCG CTCAGTAGAG GTGTTACTCT GCTCCGCTTA GTAACAAGGT | 21350 |
| GAGAACCCTG AATAAGGACC TAGGGACCAC TGACTCCAGA ACAGTGGGGT | 21400 |
| CCCAGCGTGT CACCCCTGC TGTCAGCCCT CGGAGACCCA GAGCGGGACG | 21450 |
| TGTCTCACCC TCAACTCC CTGCCCCTTA CAAAAGGGGA CCCACACGTC | 21500 |
| TCACCCTTGT GGTTGACCCT GGGAGGTCCT GTTTGAGTTC TGTCTGGAAA | 21550 |
| GGCACCCAGA GGGAGGGTCT TTCACTAAGG GAGCAGCCCC CAGTTATTCA | 21600 |
| GTTGGCGGGG ACCTGGACCC TAACTGGAGC CAAGGTGAAG TCTCCGAGTG | 21650 |
| CTAAAGGATG GGATCTGTTC CCAGTAGGGG CGTCAACAGA AAGCAGCAGC | 21700 |
| AGCCCTACTG GTTAGCATCC TCCTGGTTAG CACCAGTGGT CCTTGTCTTT | 21750 |
| TTTATTTATT TTTATTTTTT TTCAGACAAG GTCTCACTGC TGCTAGCCAG | 21800 |
| TTTAGAAGGC TCCAGACAAG TGTAGTCATA AGCGGAGGCC CTGACTTCCC | 21850 |
| CATCCAGGGA GGGAAGTGTT CAGGGAGATG AGGGTTTTGT TTGGAGGTTG | 21900 |
| GCGAACTCAG GTCAGTAGAG GAAGAAATTT CAGGCTGTGA TAAGATACCA | 21950 |
| AGGTGAAGAC CCCTGAAATG AGAATCTAGG GACCAGCAAC TCCAAAACAG | 22000 |
| TGAAGTCTCA TAGAGTTCCA CCCGTGTTGT CAGCCATCAG ACCCCAGGAA | 22050 |
| GCTGTGAACA GATAAGGCTC TTCCTCACTT CCTTGGAAGT GCTTTGAAGG | 22100 |
| GGAGGATCTG GAGGCGAGGG GCACGGGATC TCTTCGGCAG AGGGTGAATT | 22150 |
| CCTTGGACTG TCTGGAGTCA AGGTCAGGAC CCTGAATGTG CATGAAAGGG | 22200 |
| ACCACCATCC CCCAACCTGT AACAAAGAGG GCCACACTAA ATCCTGCCCC | 22250 |
| GGAAGTCTTC CCTGGGAATA CCTTGAAAGC TGTCTGACAG ATATCTACCT | 22300 |
| GGAAAGTCTC AGGGAGGGAA GGGCCTTGGT CTAAGAAAGT AGCCCCAGTT | 22350 |
| CAGCAGGTGG AAGAGAGACT TGGGTCCTAA CTGGAGTCAA GGTGAGGGCC | 22400 |

-continued

| | |
|---|---|
| CTGAGTGCTA ATGAAGCAAT CTCTCTGCAA TAGAGGTGTC AACACAAACA | 22450 |
| GTGTCCTTGC ACTCATTTTG CAACCTCCAG GCAAAGGTAT TCATAGGTGA | 22500 |
| GGGGTCCCTG ACTTCCCTGT CTAGGGTCTT GTTCTGAGGC TGGAGGACTT | 22550 |
| AGGTTAATGG AGGGAAGTGT CCCACATCCT ACTAAGAGTC AAGTCAGAGA | 22600 |
| CCTGAGAGAA AACTAAAGGG AACACTCTCT CTAAAAAGTA GAGTCCCACA | 22650 |
| AATTGTGCCT CTTCTCTCAG CTCCAGGAAG CTTTGGAATA ACGTCAGCCC | 22700 |
| CCCTTACTGC CTAGAGAGTG CCAGAAAGGT TGAACTAATT ACATGCCCCA | 22750 |
| GTTCTGCAGA GGGAAGAGTG AGGAGACCCA GAGCCTTACA GGGGTCACAG | 22800 |
| TGAGGACCCT GAATGAAGAC TAGTGATACA ACTCCTCCCA CATAAAGAAG | 22850 |
| AGACAACAAA GATTCCCCCA CTCCCCACTT GCAGCGCTGA TGAGGCTGGG | 22900 |
| CATGGAGGTC AGGTGTATGT GAACTCACCT TCTTTTAATG GCATTAGGTT | 22950 |
| GCTGAGAGCC TTTATCTAAA GTGAGGGGCA TCAGAGCAGC AGAGGCAGCT | 23000 |
| GTCCTAGGTC CTATCTAGAG ACAAGATGAG GACTATGAAT GAGGTGTCAG | 23050 |
| GACTCCAATA AGCCCAGGAA AGAGTAGGAC TCCACAATGC TGTTAGCACC | 23100 |
| CAGTTCCTCC TGTCAGGGGT GGTAAGGCTG AGACATTCCT TCACCTCCTC | 23150 |
| TTAGGTGGTC CCAAGGAGAT GAGGACATTT GCTGGAGGTG TCAAATTTAG | 23200 |
| TGCAGCACAG GGGAGAAGAC CCAGCCCTGA CAGTTTTTAT GATGGTCCTG | 23250 |
| AGTGTGAACT GAGAGAAACC TCCTACCCCA GAGTAAAAGG AGATCCACAA | 23300 |
| GGACTAGACA TGCCACGGCT GCTCTCAGTC CCAGTATACA CAGAACAGGG | 23350 |
| CTGGCAGGCT GTGGCCTAAG GCACACTTTA ATTACTTTCA CAGGGTTCTC | 23400 |
| AGAGGACAAA CTGATCAGAA CAGAAGCCTC TGGGTTTCCA GAGCAGTGCT | 23450 |
| CTCACAGAAA ACTGCAGAGG CGACCTTCTT TTAAATCCAA AGTGGTACCT | 23500 |
| CTCTGCTGAA GGCACTCATA CCCTCTCTTT CTCTCTCTCC TCCAGGTGCC | 23550 |
| TGTATCACCT GCCCTTCTGC TGACACTCCT GCCTGCTGTT CCTGACTACA | 23600 |
| GCCATCATGC CTCGGGGTCA GAAGAGTACG CTCCATGCAC GTGAGAAACG | 23650 |
| CCAGCAGACC CGGGGTCAGA CCCAGGATCA CCAGGGTGCT CAGATCACTG | 23700 |
| CAACTAACAA GAAAAAAGTA TCCTTTTCAT CCCCTCTTAT TTTGGGGGCT | 23750 |
| ACTATCCAGA AAAAGTCTGC TGGTAGGTCA CGTAGTGCTC TCAAGAAGCC | 23800 |
| TCAGAGAGCA CTATCCACCA CTACATCTGT AGATGTTTCT TACAAAAAGT | 23850 |
| CATACAAGGG AGCCAACAGC AAAATTGAGA AAAAGCAAAG CTTCTCTCAG | 23900 |
| GGTCTATCCT CCACTGTGCA GTCTCACACA GACCCTCTAA CCATGAAGAC | 23950 |
| AAATATGTTG GTGCAGTTCC TGATGGAAAT GTACAAGATG AAAAAGCCCA | 24000 |
| TTATGAAAGC AGATATGCTA AAAATTGTCC AAAAAAGCCA TAAGAATTGC | 24050 |
| TTCCCTGAGA TCCTTAAAAA AGCTTCTTTC AACATGGAGG TGGTGTTTGG | 24100 |
| TGTTGATTTA AAGAAAGTTG ATTCTACCAA GGACTCCTAT GTCCTTGTCA | 24150 |
| GCAAAATGGA TCTCCCCAAC AATGGGACAG TGACTCGTGG GAGGGGATTT | 24200 |
| CCCAAGACAG GTCTCCTGCT GAATCTCCTG GGCGTGATCT TCATGAAGGG | 24250 |
| CAACTGTGCC ACTGAGGAGA AGATCTGGGA ATTCCTGAAT AAGATGAGAA | 24300 |
| TATATGATGG GAAGAAACAC TTCATATTTG GGGAGCCCAG AAAGCTCATC | 24350 |

-continued

| | |
|---|---|
| ACCCAAGATT TGGTGAAGCT TAAATACCTG GAGTACCGAC AAGTGCCCAA | 24400 |
| CAGTAATCCT GCACGCTATG AATTCCTGTG GGGTCCAAGA GCCCATGCTG | 24450 |
| AAACCAGCAA GATGAAGGTC CTGGAGTTTT GGGCCAAGGT CAATAAAACT | 24500 |
| GTCCCCAGTG CGTTCCAGTT CTGGTATGAA GAGGCTTTGA GAGATGAGGA | 24550 |
| AGAAAGAGTC CAAGCTGCAG CTATGCTCAA TGATGGCAGT AGTGCCATGG | 24600 |
| GCAGAAAGTG TTCCAAGGCC AAGGCTAGCA GCTCTTCCCA CGCCTAGTGA | 24650 |
| AGTTGAAGCA AATTTTGCAT TTTGTGGTTA AAGAGGGCAG TCACTGTTCC | 24700 |
| AAGGAGTGAA GGACTGGGTG TTACTGGAGG AACACACTG TATAATACCT | 24750 |
| TTTGTTTCTG TTCTAAATGG ATAATTTGAA GTTTTATCTG TATTTTGGGG | 24800 |
| CATATTTTTC AAATGTTCCT TTTATTTAAC ATTGTAATCT AAGTTTAGGA | 24850 |
| TTGATACTGG TCACATTTGT TGTTTAAGAG TAAAAATTTT GCTGTTTTGT | 24900 |
| AAAACAGATT GAGAAAAATT CGATCTTATT TAGTGATCTG TTGCAAGATA | 24950 |
| ACTTGGAATT AGAATAAGCA TTTCCTTGAA AATGTTTAAA AAAAAAAGT | 25000 |
| CAGCAGTAAA ATGTATGGCA TTAAGAAATA GAGAAAGAGT GTAAGATGGT | 25050 |
| CAATATTTGG TTTCCTAAAT GCTTTTACTC TGTGTTTTAA GAAATGAAA | 25100 |
| GATAAATAAC CATATATGTC TGGCTTACTT AAGAATGTAG AATTAAATCA | 25150 |
| TAATAAATTA GACCTCATGC TGACACACTC ATTCTCCAAG TGTTAATTGA | 25200 |
| GCATCTGCTC TTGAAGGAT CCATGCTAAT ACTGGGAGGG CTAAGAAAAA | 25250 |
| GAAGACCTAG CAACTGACCT TAAAATTATA AGGTCGAGAA GCAGCTATCA | 25300 |
| TCTAAGGAAA ATGGTGATAT ACACTCTAAG ACCAAAAGGA TACATGATAA | 25350 |
| GAAGGGAGGG AGGTGGTTCC ACATGAGAAC AGTCAAGTAT GAATTATCTA | 25400 |
| ATCAAGGCGG TGTTGGGCCT AAGGAAAGTG CAGGTCCCTC AATGGGAGTT | 25450 |
| AATCTAAGTG AGGCTCCATG GTGGGCTGGA TGAGGCTGTG GGAATGGCGA | 25500 |
| GCAGGGGCCA GGCTCTTAGA AGTTGCCTCT CACGCAGTGC GGGCGCCTGT | 25550 |
| AGTCCCAGCT ACTCGGGAGG CTGAGGCAGG AGAATGGCGT GAACCTGGGA | 25600 |
| GGCAGAGCTT GCAGTGAGCC GAGATTGTGC CACTGCAGTC CGGCCTGGGC | 25650 |
| TAAAGAGCGG GATTCCGTCT CAAAAGAAAA AAAAAAAGAA GTTGCCTCTC | 25700 |
| AGAGGTGCGA GACAAAGCTT GGAATAGGAA ACAGTTCTTA ACAGTTACTT | 25750 |
| TGGGATCATG GATAAATCAG GGAGAATCTG GGTAGGAAT GTGTCCTGTG | 25800 |
| CTCTTGTCCC AGTACAAATA AACACAGCAC ACACTAGGTG TTTTGTGCAC | 25850 |
| ATCATCTCCA GCCAGTTTCT GAGAAATAAG GGTAATACCC TCAAGGGACG | 25900 |
| GGGGAGGCCC AGAAGCCACT GTGCTGGTAC TCTTTGCCCT GGGCTGGGGG | 25950 |
| ATCCAGAGCC TGTTCCATTA AAAGCGCATT CAATTAGGTT ACCTCATTTG | 26000 |
| TGATTTGGCA GACTCTAGGC AAGTTCTAGA TTTTGAGAGG TGGTTAAATG | 26050 |
| AATCAAAATA AAAGTGGTTT AGATGGAAGG ATAGCTGAGA GAGAGGGAAG | 26100 |
| TTTTTGGTCC TTGAAACTCA TTTTAGAATC TGTGTTGCAT CTACTGAGGA | 26150 |
| AGTCTACCTC ATACTAATAT TGAATGATCT ATCAAGTAAT GAGGAAATAT | 26200 |
| TATTTAGTTT TCCTTTCTAG GTAGCACTTT GTCTGATAGG GCTTTCTTTG | 26250 |
| TCTTAGAATA TGGTATAATC TCTGACATCT CCTGCATTGA AAAATAAGTC | 26300 |
| CCAGTGTAGT AGATTGCAAC GTCAGGGTAC AAATTAATCA TAATAAGAAC | 26350 |

| | |
|---|---|
| TGGCACTATT ATATGTCTCA ATACATCTCA AGCACTTTAC ATACATTGTA | 26400 |
| TACATTTTAC CAGTCCTACA AAACAGAGCT TATCAAACCC ACTTCACAGA | 26450 |
| TAAAAAGCCT GAAGCCCACA GTCTATTAAT ATGTCCAATT TCACATGGCT | 26500 |
| GGTAAGTGAC AGGACTGGGA CAAGACCCCC AGTCTGAATT AGTGTAAAGC | 26550 |
| ACACTCTGTT CCATGCCTCC CAACCTGAGA CTGACTGTGT CCCCTTATTC | 26600 |
| ACTTTTCTTC TCACTACTCC CAAACGTATA TCAAGTGATG AAAAGATTCT | 26650 |
| GTACCCAATC TGCTGGACTG AAATACAGAA CCAGAGCAAG GAAATTACCA | 26700 |
| AAATGGTCAA GAGGTGTGAA TTAAGGAGAG AAGATAATAT TTGGTGACAA | 26750 |
| TAAGATTACA CATGCAAAGG CAGATAAACT CAAAAGTCAT GGGGTCACAT | 26800 |
| TCTGGCAATC TGGACTGGCC CCCCTTTTAT AGGAAGGTAA ATCCTTTCCA | 26850 |
| AGAGAAATAC ATAAGAGGGT AGTAAAGAGA AGAAATAGGA TCAATGGTTT | 26900 |
| TTTTTTTTTT TTTTTTTTCT CTGACAGTAT GACTTCTATC CTCGGCTTCT | 26950 |
| GCCTTGTGTT ACAGCTTCCC TATCTTATAT CACTCCTGGG ACAGGGATGC | 27000 |
| ATTGTCTGCA AGATTTATTA TAGGGAAACT GATCAAGAAT TTTTAGGGAT | 27050 |
| GCGGCATTTC TCAGGAAGTC ATTAACTAAG GGACAAGAGC CAAGATAAAG | 27100 |
| ACCTTCATAT AGGAGGACTC AGCAGAACAA CATGCCAGAC AGAGTTCTTA | 27150 |
| GCCTGAGCAT CTCCTCACTT ATTCTTCAAG GTTCTCAGGG ACTTGTGAGT | 27200 |
| TCCGCATCTC AGGTCAGTAG AGGGAGGAGT GCCATTCTCT GACACATACC | 27250 |
| AAGTTGAGGA CCCTGAATGA AGAATGAGGG AAGCACTCAC CCAAATAGCC | 27300 |
| TTAACAGGAT GTGGCTGAAC CTGATTTCTA CTCCGGAGGT CTTAAGAAGG | 27350 |
| TAAAGACCAT GATCTGAGGC TGGCTGACTC AGGTCCATAG AGGAAGGATT | 27400 |
| CCTAATGTGT GCCAGGAGTA AAGTGAGTAC CCTGAAGAGT GCAGGAACCA | 27450 |
| CCAAACCCCT ATCAGTGGGA TCCCACAGAA TCCTCCCTAT TGTCACCTCT | 27500 |
| GAGAGATTTA GGCATGAATG TCAGAAAGAG GCACCCTCAT ATCCTCAGTA | 27550 |
| GTAACAGAGA AGTGAAGGTC TTGTTCTGAG GTGGGCAATC CCAGCTCAGC | 27600 |
| AAAGGGAGGA ATATTAAGCC TTCCTGTGAG TGAGATTTAG GATCCTGAGT | 27650 |
| TAGGACCTGA GTAGGACAAT CCACCATAAG ACCTCAACCT GTCTACCACA | 27700 |
| GCTGCCACTC TTGGGAGACC ATGGTCAGCT GTGCCAGATA AGGCCACCCT | 27750 |
| CTTCCTCCTA TCAGATCTCA GGGAGTGCAG CCTTTTTAAA TGGAGAGTCT | 27800 |
| TCAGTCAAAA AAGAGGGGAG CCCTAGGATC TGCTAGGAGC CAAATCAAGG | 27850 |
| AAACCGAGTG AGAACTGAGG GGACTGCTCA CCTCTGAATA GAGAGAGCAA | 27900 |
| CAGAGTCCAC CCCCCTGCAT AACTCTTAAA GTGCCAGGGC AACATGTAAG | 27950 |
| GCTGAGGACT CACCATCACT TTTTTTTTTT TAATAATTGA CCTTCTTTTT | 28000 |
| TAGAATAGTT TTACGTTCAC AGCAAAACTG AGCAGAAAGG AGAGTCTCAC | 28050 |
| AGGCATCCTG TCCTCCCACA GACACAGCCT CCTTCATATC AACCTCCCAA | 28100 |
| GCCAGGGTGA TACATTTGTT ACAATTGAGA ATACATGGAC ACATCATTAT | 28150 |
| CACCCAATGT CCGTAGTTTA GGATTCATTC CTGTTGCTGC ACATTCTGTG | 28200 |
| GTTTTAATAT TTAAAAATGT ATAATGACAT ATGTTACCAC CATAGAATCA | 28250 |
| TCCAGAAATT GTTTTACTGC CTTAAAAGTC TCTGTGCCTG ATCTATTTAT | 28300 |

-continued

| | |
|---|---|
| CTCTCACTCT CCCCAACCTG TGGAAACCAC TGAACTTTGT ACTGTTTCCA | 28350 |
| TACTTTTGCC TTTTCCAGAA TGCATATAGA TGGAATTATG CAATGTATAG | 28400 |
| ACTTTTCAAA TTGGCCTCTT TCACTTTGTA ATATGTATCT AAGTTTCATC | 28450 |
| CATGTCTCTT TGTGGCTTGA TAGTTCATTC CCTTTTAGTG CTGAATAATA | 28500 |
| TTTTATTCTG TTAATTTATC CACTCTCCTT CTGAAGGACA TATTGCTTGC | 28550 |
| TTCCCAGTTT GGGCAATTAT GAATAAAGCT ACTATAAACA TTTGTGTGCA | 28600 |
| GGTTTTTTTT GTGGACATAC CGTTTTCAAC TCATCTGGCT AAATAACAAG | 28650 |
| GAGCGCACTT GCTAGATCAT ATGATGAAAG TATGCATAGC TTTGTAAGAA | 28700 |
| ACTTACAAAC TGTCTTCAAG AGTGGCTGTA TCATTTTTCA TGTCCACCAG | 28750 |
| CAATGACAGT GTGCTCCTGT TGCTCCACAT CCTCATCAGT ATTTGGGGTT | 28800 |
| ATCAGGGTTT TTGATTTTGA CCATTCTTAT AGGTATGTAG TGGTATCACA | 28850 |
| TTATTGTTTT AATTTGCAAG TCTCTAATGA TATGTGATGT TGACCATCAT | 28900 |
| GTCATGTACG TATTTGCCTT CCATATATAT TATTTGTTGA GGTGCCTGTT | 28950 |
| TAGATCTTTT GTCCATTTTT AATAGGGTTG GTCAGTTCTT ATTGTTCAGT | 29000 |
| TTTAAGACAT TTTTGTATGT TTTGGTTAAC AGTCCCTTAT CAGATATGTC | 29050 |
| TTTTGAAAAT AATTTTTTCC CAACCTGGGA GTTATCTTAT TCTCTTTGTG | 29100 |
| GTATCTTTAG CAGAGCAGAA GTTTTAATTT AGCGAAGTCC AGATTATCAA | 29150 |
| TTATTTTCTT TCATAGATGC CCATCACATT TTATACCAGA ACTAGAAAAG | 29200 |
| ATGAAATTCT TGGTCTGAAG TTGCAGTTAT CAGTCAGCAG AAGAGACAGT | 29250 |
| CCACAACCCT GCTTGGAGTC CAGATGAGGA TCCTGAGTGC AAACTTGGGA | 29300 |
| CCTAAAGAGC CCAGGACAGA GAGAGCACTA AATGCTTCTA GGCAGGGGTG | 29350 |
| GTGGGTTGAG GGGCCCCTAG ACTTCCCTCA TCTGGGTCCC AGAAAACTAA | 29400 |
| AGAGTCAATT TCACAACACC AATAGAGGGA GGCTCAGGCC CTGCCAAGAG | 29450 |
| CTGACATGAT AATTCTAAAG GTAATCAGAG TGGATCCTCT CCAAGCCAGA | 29500 |
| ACACAGAAAG CCCCACTGCG AGCCTTGTTG TCACCCAGTC AGCCCCAGGC | 29550 |
| AGGGTTGGCA AGCTGCAGCC TAAGGCACAT TGTAACTTCC TCAGCTGGCT | 29600 |
| TCTCAGGGGA CAGAATGACT AAGAACAATA GCCCAGTGAA TACTTAGAGC | 29650 |
| AGTGTTCTCA AGGAATCCTG CAGAGGCGGC TTCTGAAAAG CCAAGGTAGT | 29700 |
| ATCTGCCTGC TGAAGGTGTT CTCAGGATTT CATTTGCTCT TCTCCAGGAA | 29750 |
| CCACATCACC TGCCCTTCTG CCTACACTCC TGCCTGCTGT GCCTAACCAC | 29800 |
| AGCCATCATG CCTCGGGGTC AGAAGAGTAA GCTCCGTGCC CGTGAGAAAC | 29850 |
| GCCAGCGGAC CCGTGGTCAG ACCCAGGATC TCAAGGTTGG TCAGCCTACT | 29900 |
| GCAGCAGAGA AAGAAGAGTC TCCTTCCTCT TCCTCATCTG TTTTGAGGGA | 29950 |
| TACTGCCTCC AGCTCCCTTG CTTTTGGCAT TCCCCAGGAG CCTCAGAGAG | 30000 |
| AGCCACCCAC CACCTCTGCT GCTGCAGCTA TGTCATGCAC TGGATCTGAT | 30050 |
| AAAGGCGACG AGAGCCAAGA TGAGGAAAAT GCAAGTTCCT CCCAGGCCTC | 30100 |
| AACATCCACT GAGAGATCAC TCAAAGATTC TCTAACCAGG AAGACGAAGA | 30150 |
| TGTTAGTGCA GTTCCTGCTG TACAAGTATA AAATGAAAGA GCCCACTACA | 30200 |
| AAGGCAGAAA TGCTGAAGAT CATCAGCAAA AGTACAAGG AGCACTTCCC | 30250 |
| TGAGATCTTC AGGAAAGTCT CTCAGCGCAC GGAGCTGGTC TTTGGCCTTG | 30300 |

| | |
|---|---|
| CCTTGAAGGA GGTCAACCCC ACCACTCACT CCTACATCCT CGTCAGCATG | 30350 |
| CTAGGCCCCA ACGATGGAAA CCAGAGCAGT GCCTGGACCC TTCCAAGGAA | 30400 |
| TGGGCTTCTG ATGCCTCTAC TGAGTGTGAT CTTCTTAAAT GGCAACTGTG | 30450 |
| CCCGTGAAGA GGAAATCTGG GAATTCCTGA ATATGCTGGG GATCTATGAT | 30500 |
| GGAAAGAGGC ACCTTATCTT TGGGGAACCC CGAAAGCTCA TCACCCAAGA | 30550 |
| TCTGGTGCAG GAAAAATATC TGGAATACCA GCAGGTGCCC AACAGTGATC | 30600 |
| CCCCACGCTA TCAATTCCTG TGGGGTCCAA GAGCTCATGC AGAAACCAGC | 30650 |
| AAGATGAAAG TCCTGGAGTT TTTGGCCAAG GTGAATGACA CCACCCCCAA | 30700 |
| TAACTTCCCA CTCCTTTATG AAGAGGCTTT GAGAGATGAA GAAGAGAGAG | 30750 |
| CTGGAGCCCG GCCCAGAGTT GCAGCCAGGC GTGGCACTAC AGCCATGACT | 30800 |
| AGTGCGTATT CCAGGGCCAC ATCCAGTAGC TCTTCCCAAC CCATGTGAGA | 30850 |
| TCTAAGGCAA ATTGTTCACT TTGTGGTTGA AGACCTGCT GCTTTCTCTG | 30900 |
| TTCCTGTGAT GCATGAATAA CTCATTGATT TATCTCTTTG TTGTATTTTC | 30950 |
| CATGATGTTT CTTAAAATAG AAAGTTTATT TAGATTCAGA ATATAAATTT | 31000 |
| AGAAATGGCA TGCATCACAC ATTTATTGCT GTTTATCAGG TTGGTTTAGT | 31050 |
| GATAATAATT TTGTTTTTGA AATACAAATA GAAAATCCTG AAATAATTTT | 31100 |
| TGTGATACAG AGCAAAATAA CACGGCATGG GAGTAAGGTT ATCCTTAGAA | 31150 |
| ATTTAAAATA ACTCCACAGT AAAATAGGTA GAATCTGAAG ATAGAAAGGG | 31200 |
| AAGAAAAGTA AAAGTTGCTT TATTCGTGGT TTGTCTTACT CAGTTCAGTC | 31250 |
| TTTTTTTGCT CATAAATTTA AAAGTTACAT ACCTGGTTTG CTTAGATTAT | 31300 |
| TCAAGAATGT GGAGGCCTGG GCCAAGGTCA ATGACAGTGT CTCCATTGTC | 31350 |
| TTCCCTCCAT TAAGAGAAGA CTTTAAGAGA TGAGGGAGAG AGAGCCAGAG | 31400 |
| ACAGTGTTGC AACTGGGCCT GGCATGTTTC AGTGTGGTGT CCAGCAGTGT | 31450 |
| CTCCCACTCC TTGTGAAGTC TGAGGTATAT TCTTTACTTT TGATTAAGAA | 31500 |
| AACACTTAAC CTTCTAATTA ATGGAGAGCC AAAGGGGAGT TGGTGGGAAC | 31550 |
| ACCATGTATA ACATATTTGT ATGTAAAATG ATTTATCTTT TCTTTTTCCT | 31600 |
| GTTTTTCAGT GTTCTTTTTT TAAATTGTAG ATTTATTTAG TTTCAGAATC | 31650 |
| TAAGTTTATG AATGGCATGA ATCACTCATT TATTAAAATA TATCAGGTTG | 31700 |
| GAGAGTGAGA ATTTTTGCAT TATGTAAAAC AATTTAAAAA TCTTTTAAGT | 31750 |
| CTTTTTCTGT GATCTAGAAC AAGATAATAT GGCATTGGAA TATGGAATTT | 31800 |
| GTGAAAAGGA AATTACCTTG CAATAAAGTT GGTGGGACCA GGAAGTAGAG | 31850 |
| AAAAAAAAAG TAAAATGTGG TCAATTCTTG CTTTGTTTTA TTCTTTTTAG | 31900 |
| TCTTTCTTTG TAAAACTGAA GTATATGTAC CCGGATCTGC TTAGCTTTTT | 31950 |
| CAGGAATGTG GGGAAATTA AATAGCAATA CATTTGACTT CCTGGTCACT | 32000 |
| TACACTTCAA TTGTCCAAAT ATTAATTGAG CAGCTGTACT TTGGAGGGCT | 32050 |
| CCTGGCTAGT ACCGGATAAG CTAAGAAAAC AAAAACAAA CAAACAACAA | 32100 |
| AAAAACCCCA ATCCCTGCCC ACAGAATTTT AGAATCCAAC AGCAGCTATC | 32150 |
| ATATAACGAA GGTAATGAGA TACTCCTTAA GACCTAAAGA CAGGTGAAAA | 32200 |
| GGGGATAAAA AAGAAGGTGG GGGTATTACC AGCAGTGAAT CTAGTGTAAA | 32250 |

| | |
|---|---|
| TGTCCTAAGC AAGGTAACTG AGACTTCGGG AAACTGAACA TACTGCAATA | 32300 |
| GGAGGTAATT TTATGTCCTG GCATAGTGCC TATATGGGGC GCACTGAGCA | 32350 |
| GGGGTCACAC ACTCAGATGG TGGATCTCAC ACTTGAGAGA TGGAGACTGG | 32400 |
| AATGAAAAAT TGCCTTTAAC AGTTACTTTG GGATTGTGGA AAAACCAGAG | 32450 |
| GGGATCTTTG CCTGGAGCAG GGATTGAAAG TGGCCGGTGC TCTTGTCCCA | 32500 |
| GTGCAAGTGA AGTGAATCCA GTACACAACT AGGTGTTTAT GAGCGTAGTC | 32550 |
| CCCAGGGTGT TCTGAGAAAT AAAGGTGATA CTCCTTTAAG ACTGGAAACT | 32600 |
| CATAAGCCAC TGGGCTAATA CTCTGCTATC AGCTGGGAG CCAGAACCCA | 32650 |
| TTCCATTAAA AGGAATTTTT TTTCCTTTCA TGTGTTTTTG CAAATTCTAA | 32700 |
| GGGAGATCTA GATTTTTGAT GGTGGTAAAA TGAATGAAAA TAAGACTGGT | 32750 |
| TTGGATGAAA GGCCAGAGTT GGTCCTTGAA CCAAAGCCTA GAAGGTTTGA | 32800 |
| GTTGCTTTCA GCTGAGAAAG ACAACTCCAC ACTCAAAATA TGATTTAATA | 32850 |
| TGGAAAAGTT ATTTAGAGTT TCTTTGTAAG CTGCGTTTTG GGCTGATTTT | 32900 |
| ATTGTTCCAT GTCTTAGAAT GCTGTATATT CTTTGTTATC TCTTGGACTT | 32950 |
| AAAGAAAATC AGCAGGGTGG ATGATTTCTT CTGTAGTTGA AATAATCTTA | 33000 |
| GTAATAACAA GTATTGTTTA AAGTCTCAAT GCACACCAGG GCTTTGCACA | 33050 |
| CTTTCACCAC ATTCCACCAG TCCTACAAGA CAAGGCTTAT CAAGCTCATT | 33100 |
| TCACAGATGT AGAGCCTGAG GCTCATAGAG TTTATTAATT GTGCCCAAGT | 33150 |
| TCACACAGCT AGTAAGTGAT AGGGCTGGAA CTAGACTGCT GGTCTGAATT | 33200 |
| CCTCTAGAGC CCACACTGTT CCACTCCTCC CAAACTGAAG CTTACTGTGA | 33250 |
| ATTGCTTAAT TCATTTTCTT CTACAACCCC AAAGTGTGTC TCAGGTAAGA | 33300 |
| AAGAAGAGGT CTCTGTACCC CAAACACTGG ATTGGAATAC ATAACCAGAG | 33350 |
| CAAGAAGAAT ACCAAAATAA TTGACAGATG TGAATTAAAG AGAAAAGAA | 33400 |
| ATAATACTCG GTGACAATAT GATCACCGAC AGAAGCAAAA TTGGATAGCT | 33450 |
| TCAAAAGATC AAAAGATTAC AAAAATCATC TGGCTCCACC CTTTTCTGTA | 33500 |
| GAAAGTAAAA CTTTTAGAAC TACCCTTTGG TTGGTGAAGT GAAGGAATAG | 33550 |
| ATCAGCATGT TTTTTTCCCT GAGAGCACAA CATCTGTCCT AGGCTCTCCA | 33600 |
| CCTTCCGTTT CAGTTTCCCA ACATCACATC ACTTCTGGGA CAGGGACCTC | 33650 |
| TTCTCTGCAA GGTTTGCAAA GAGGAAACTG GTCAAATTTT TGCAGGGATG | 33700 |
| TGACATTTCC CTGGAAGAGT TTGATCAAGA GACAGAAGCC AACATGAGAA | 33750 |
| CCCTCATGAA TGAATGGTGG GGAGAAAACC ACTCCAAAAT GTAAGGGTTC | 33800 |
| ATCCAGACCC TCAGGAGAGT GACCTCAGTT CAGTAGATAG AGGAGTCCCA | 33850 |
| GGTTCTGATA CATGTAAAGG CGAGGAGCAT AAATGAAGAC TGATGGAAGG | 33900 |
| ACCCAGCCAA AACTGTGGGG TTCTATGGAG TCCTTTCCTT ATTATCTGTT | 33950 |
| TTTGCAGGTT GCAAAAGGAC TGTGATCATA TGAAGATCAT CCAGGAGTAC | 34000 |
| AACTCGAAAT TCTCAGAAAA CAGGACCTTG ATGTGAGAGG AGCAGGTTCA | 34050 |
| GGTAAACAAA GGGTAAGTTA CAGGTTTGCT CACTTGTCAA GGTGAGGACC | 34100 |
| TGAATGTGGA CTAAGGGTAG CTAGCACCCA CATGGCCTCA CAAAGTCCCC | 34150 |
| TCTGCCTGTC AGCCCTAGGA AGCCTTGGCG AGATGGCAGG CTGAATTCTG | 34200 |
| CCTGGAAAGT CTCAGGGAGA TGACTGGTTC CGTCTAATTG GGGCAGCCTC | 34250 |

| | |
|---|---|
| AGTTTTACAG AGCGAAGAGG CCGAGACCCT AACAAGAATC AATGTAGGGC | 34300 |
| TTTTAAGTGT TAAGAGGGGT ATCCACCAGC AGATGAGTCC CCACAGAATT | 34350 |
| CACCCCGTTT TGAGGCATCA GACAGAGCTA TCTACCTAAG GTGCCTCTCA | 34400 |
| TTTCCGCCTG GAAGGTCTCA TGGAGGATGG GGAGCGTGGG GCCTGAAGGG | 34450 |
| AGTAGCTTCA GTTCTGCCTG GAGAGGAAAC CAGAGTCACG GTGAGGACTC | 34500 |
| TGAGAGCTGA TGAGAAGGCC TCTGCCCAAA ACGGGACTTT CACAGAGCCC | 34550 |
| TGCCGCTGCT GTCAGGCCTG TGAGGCCAGG CAGGGGTGGC CTGTGTGGCA | 34600 |
| CGCTCAGATT TCCACCTTGG GGGCTGAGAG AGGTGGGGCT ATTGTTTGAG | 34650 |
| GCTGGCGGAT TTGGGTCAGC AGGCGGAGTC GTCCCAGACT GCTAGATACT | 34700 |
| AAGGTGAGGA CCCCTAGTGG GGACGTAGGG ACCAGCGACG CTAGAACAGT | 34750 |
| TACGTCCAGA AGCGTACCAC CCCTGCCGTC AGCCCGGAGC CACGGGCTGC | 34800 |
| CGGATGTGGC TCATCCTGAC TTCCGCTTTG AAGGCGAGGA CCCCAGCGAG | 34850 |
| CGTAAGGGCG CAGTGTCCGC CTGGCGGATT TGGGTCAGCA GGCGGAAGTC | 34900 |
| GTCCCAGGCT GCTAGATACT AAGGTGAGGA ACCCTAGTGG GGACGTAGGG | 34950 |
| ACCAGCGACA CTAGAACAGT GACGTCCCGT AGCGTCCTGC CTCTGCCGTC | 35000 |
| AGCCCTCAGA GGCCCTGGGC TGCCGGATGT GGCTCATCCT CATTTCCCTT | 35050 |
| TTGAAGGCGA GGACCCGAGC GAGCTTAAGG AGTGGGGTGC AGCGTCTGGT | 35100 |
| CAGCCGAGGG TGAATTCTCA GGACTGGTCG GGAGTCAAGG TGAGGACCCT | 35150 |
| GAGTGTAAAT TGAAGAGACC ACCCCCACCC GTAACAAAGA GGTCCCCTCT | 35200 |
| AAGTCCCGCT TCTGCATTTG GTCCTGGGAG GCCTCAGGTA ACCAGATGGG | 35250 |
| TAGCACCCTG ACTGTCTCTT CAGCGACTCA GGGAGACGAA GGCTTTGGCC | 35300 |
| TAAGCCTTAT AGACTCAGGT CAATAGAGGG AGGAGTCCTA AACCCTACTA | 35350 |
| CCCGTAATCC CAGAACTCTG GGAGGCCGAG GCAGGCGGAT CACGAGGTCA | 35400 |
| GGATATCAAG ACCATCCTGG CTAACACGGT GAAACCCCGT CTCTACTAAA | 35450 |
| AATAGAAAAA ATTAGCCAGG TGTGGTGGTG GGCTGCTGTA GTCCCAGCTA | 35500 |
| CTCAGGAGGC TGAGGCAGGA GAATGGCGTG AACCAGGGAA GCGGACGTTA | 35550 |
| CAGTGAGCCG AGATTGCACC ACTGCACTCC AGCCTGGGTG ACAGAGCGAG | 35600 |
| ACTCAGTCTC AAGAAAAAAA AAAAAAAAAA AAAAAAAAA AAAGTCCCGC | 35650 |
| TCCTGCTGTC GGCACACGCA GGCCCCAGTC AGCCTTGGTG GGATGTGGCC | 35700 |
| CACTATGACT GTGAACTTAG GTCCAAGGAA TATGAGAACT TTTGTCTACG | 35750 |
| GGGCATGGTG TTAGGAGCAG TTGATGGGTG GAGTCCCAGA AAGAGTGCTG | 35800 |
| AGTGGAGGTG GAGACACTGA GTGAGGAAAT GGCGGCTACT CTATACACGA | 35850 |
| GGGAGACAAT TGCGCCTGAT GCTGTCCCTG GGAGTCCCAG CCAGAGCTG | 35900 |
| GCAGGCTCAA GTCTCCCTGG CTTCTGCCTT CATGGTCTTA GAGAGAGGAG | 35950 |
| GGCCTTGGTT TAAGGCCTCA CTGCCCCAGT TCAGTAGAGA GATAGGAGTC | 36000 |
| ATACGCCAAG ACAGGTGTCA AGGTACAATT TCTTTATGAG GAATGAGGTA | 36050 |
| ACCGTCTAGT CCAGCAACAG GCAGGAACAC AGTCTTACCT TGGCGTTCAT | 36100 |
| TCCTTAGAAG CCAGGGTTAG ACTCTCAAGT TGAGATGCCC CTCATTTCCT | 36150 |
| TCAGGTACTG TTTCAGGTAC ATAATGGCTT TGGTTTAACA TGAAAGCCCT | 36200 |

| | |
|---|---|
| TGTTTAGTAC AGGGAGGAGG CCCAGTTCCT AAAAGATGGT GACACTGAGG | 36250 |
| GAGTATGAGG GGACCCCCTC CAAGAAAGAG GTAACACAGA TAGAGCCCTA | 36300 |
| TCCCCACTGA GACCTGGGAG ATCCAGGTAT GGTGACATGA TGAGTCTCAC | 36350 |
| TCACTTCTTC CTAGAGCATC TCAGGAAGTG GGAACTTCAT CAAAGGGGGC | 36400 |
| AGCCTTATGT TAGCAGCTAG AGATTCCTAG TAATTCCAGG AGTCAAAAGA | 36450 |
| AGACCCTGAG AACTGGGGAA CCACTCATCC CATAACAGTG AAAGAAACAC | 36500 |
| GGAATTCCTT CCTGATTTTC ATCCTTGGGA GATGATGGCA AATTGTAGCC | 36550 |
| AGATGGGAAA AGTTTCACTT CTTCCTCAGG GAGTTGTCGG GGGGTGCTTT | 36600 |
| GTATGACTGG ATAGGCGTTA GATCAAGACA GAGAAGTCAC TGAGGGAGGA | 36650 |
| ATGAGATGAG CATTTACCTA GAGAGTGGGC TTCACCAAGT TCTACCCCCT | 36700 |
| CTCAGCTCTG GGAAACCCCA GGCAGAAGTA CCCAGATGTG TCATCCCCTC | 36750 |
| AAGACTAGCC CTGGGTACTC AGAGAGGTGA AGGCTTTTGT ATGAGCCTGG | 36800 |
| AAGAATCAAG TGGGATTAGA GAGGAGCTCA GACTCTGCTT GAGTGAAGAC | 36850 |
| TAAAGAGAAC AACGACCCCA GAACAGTGGA GCCCCATAGA GGACGTGGTG | 36900 |
| ACTGGATGTG ATTCAGGCTT TCTTTCATCT TGGGACTATG AGGCAATGAG | 36950 |
| AATCTTAATC TGATGTAAGG GGCCTCAGGT CAGTAGAGAG AGGATTTCCA | 37000 |
| GGTTGTGCCA GGCCTCATAG AGAGGACTTG AGGGAACTCC CACCTCATCA | 37050 |
| GTGGGGATCC CTCAGAGTCC CTCTGTATGT CAGCGCTAGG AAGCCCCGAG | 37100 |
| CATAAATGTC AGAAATGCCC CTAAATTCCT CTTCAGAAGT AACAGGGAAA | 37150 |
| TGAAGGTCTT AGTCAGATGG GTTAGCAGGA GGGGTGGGAG GCATTTTAGG | 37200 |
| CCCTCCCAGG AGTCAAACTG GAGACCTTGA GTGAGGACCA TGAGTGGGGC | 37250 |
| TACACATCAC AGGGCTTCAA CCTGCCAGCC ACAGCTTTCA GCCTCTGGAG | 37300 |
| AATATGGGCA TTGTGACCAG ATACAGCCAC CCTCATTTCC TCCATTGGGT | 37350 |
| CTCAGGCAGA TGTAGGCCTT ACTATAGTA AATGTCCTCA GGTGTAGAGA | 37400 |
| GAACAGAGCC CTAGGCCCTT CTGGGAGTCG AAGTGTGAGT GTGGACTGAA | 37450 |
| GGCACCATTC CCCCAAGCCC CCAACCCCCA CCCCAAATAG AGGAAAAACA | 37500 |
| ACGATGCTAG CCCTGTCTCT GCACTTAGCT CTGAAAGGCC TTGGCCAAGG | 37550 |
| GTTGCCAGGC TGAGACTTTA TTTCTTTGCA TCAGGTCTAA GGGAGGTGAC | 37600 |
| AGCTTTGGTC TGAAGATGCA GCACCAGTTA GCAGAAGACA GGTTCCCAGA | 37650 |
| ACTTAGATAT AGATGAGATG AGGACTCTGA ATTAAGATTG AGGTCCAACT | 37700 |
| AGCCCAGGAC AGAGAGAGTT CCATAGAACT GTCAGCACTG CCATCCCGCC | 37750 |
| AGCCCCCGGT AAGGATGGTA GGTTGAAGCA GTGCCTCATT TTTCTTTGTG | 37800 |
| GATTCCAGGG AGCTTTGAAG TGTCAGCTTC AGAGCAGCAC AGGAAGGAGT | 37850 |
| CCCAGACCCT TCCAAGAGTA GATATGAAGA TCCTGTATAT GAATTGAGAG | 37900 |
| GCCTTGAACA CAGAGGAGTC TACACTGCCA ACCTCTGCTG TCACCCAGTC | 37950 |
| AGCCCAGGCA GGTTTGGCAA CAAGAACCAG TGGTTCCTAG AGCAATGCCC | 38000 |
| TCAAGAAAAC CAGCAGAAGT GCTCTCTAAA AGCCAAGTTG TACCTCCCTG | 38050 |
| CTGCAAGTAC TCACAGATCT CATTCTCTCT CCTTCAGGTG CCACATCTCC | 38100 |
| TGCCTTTCTG CTCACTTTCC TGCCTGTTTT GCCTGACCAC AGCCATCATG | 38150 |
| CCTCGGGGTC AGAAGAGTAA GCTCCGTGCT CGTGAGAAAC GCCGCAAGGC | 38200 |

| | |
|---|---|
| GCGAGAGGAG ACCCAGGGTC TCAAGGTTCG TCACGCCACT GCAGCAGAGA | 38250 |
| AAGAGGAGTG CCCCTCCTCC TCTCCTGTTT TAGGGGATAC TCCCACAAGC | 38300 |
| TCCCCTGCTG CTGGCATTCC CCAGAAGCCT CAGGGAGCTC CACCCACCAC | 38350 |
| CACTGCTGCT GCAGCTGTGT CATGTACCGA ATCTGACGAA GGTGCCAAAT | 38400 |
| GCCAAGGTGA GGAAAATGCA AGTTTCTCCC AGGCCACAAC ATCCACTGAG | 38450 |
| AGCTCAGTCA AAGATCCTGT AGCCTGGGAG GCAGGAATGC TGATGCACTT | 38500 |
| CATTCTACGT AAGTATAAAA TGAGAGAGCC CATTATGAAG GCAGATATGC | 38550 |
| TGAAGGTTGT TGATGAAAAG TACAAGGATC ACTTCACTGA GATCCTCAAT | 38600 |
| GGAGCCTCTC GCCGCTTGGA GCTCGTCTTT GGCCTTGATT TGAAGGAAGA | 38650 |
| CAACCCTAGT AGCCACACCT ACACCCTCGT CAGTAAGCTA AACCTCACCA | 38700 |
| ATGATGGAAA CCTGAGCAAT GATTGGGACT TTCCCAGGAA TGGGCTTCTG | 38750 |
| ATGCCTCTCC TGGGTGTGAT CTTCTTAAAG GGCAACTCTG CCACCGAGGA | 38800 |
| AGAGATCTGG AAATTCATGA ATGTGTTGGG AGCCTATGAT GGAGAGGAGC | 38850 |
| ACTTAATCTA TGGGAACCCC GTAAGTTCA TCACCCAAGA TCTGGTGCAG | 38900 |
| GAAAAATATC TGAAGTACGA GCAGGTGCCC AACAGTGATC CCCCACGCTA | 38950 |
| TCAATTCCTA TGGGGTCCGA GAGCCTATGC TGAAACCACC AAGATGAAAG | 39000 |
| TCCTCGAGTT TTTGGCCAAG ATGAATGGTG CCACTCCCCG TGACTTCCCA | 39050 |
| TCCCATTATG AAGAGGCTTT GAGAGATGAG GAAGAGAGAG CCCAAGTCCG | 39100 |
| ATCCAGTGTT AGAGCCAGGC GTCGCACTAC TGCCACGACT TTTAGAGCGC | 39150 |
| GTTCTAGAGC CCCATTCAGC AGGTCCTCCC ACCCCATGTG AGAACTCAGG | 39200 |
| CAGATTGTTC ACTTTGTTTT TGTGGCAAGA TGCCAACCTT TGAAGTAGT | 39250 |
| GAGCAGCCAA GATATGGCTA GAGAGATCAT CATATATATC TCCTTTGTGT | 39300 |
| TCCTGTTAAA CATTAGTATC TTTCAAGTGT TTTTCTTTTA ATAGAATGTT | 39350 |
| TATTTAGAGT TGGGATCTAT GTCTATGAGC GACATGGATC ACACATTTAT | 39400 |
| TGGTGCTGCC AGCTTTAAGC ATAAGAGTTT TGATATTCTA TATTTTTCAA | 39450 |
| ATCCTTGAAT CTTTTTTGGG TTGAAGAAGA AGAAAGCATA GCTTTAGAAT | 39500 |
| AGAGATTTTC TCAGAAATGT GTGAAAGAAC CTCACACAAC ATAATTGGAG | 39550 |
| TCTTAAAATA GAGGAAGAGT AAGCAAAGCA TGTCAAGTTT TTGTTTTCTG | 39600 |
| CATTCAGTTT TGTTTTTGTA AAATCCAAAG ATACATACCT GGTTGTTTTT | 39650 |
| AGCCTTTTCA AGAATGCAGA TAAAATAAAT AGTAATAAAT TATATTACTT | 39700 |
| GTTCAGTGGC TCATTTATTC TCACCATAAA TTGAGCATCT GCTCTTTGTA | 39750 |
| AGGCTCTGTG ATAGTAGTGA TTGTACTAAG TTAAAGAAGA CCCTTCGCCT | 39800 |
| GCACACAGAT TTTTAGTCTA AGGACAGTTA TTATTTAAAG AAGATGGTGA | 39850 |
| GATACACTCT AACATGTACA GATTTTTTTT TTTACATATA AACACTCATT | 39900 |
| TAAAAAAAAA AGAAGTGAGA ATGGTGGGAG AAGGTTCAGA CAAGAGCAGT | 39950 |
| CAAGTGTTAA TTTCCTAGCC AAGGCACTTC GTGGTGTGGG ACAATGCAAG | 40000 |
| TCCCTCGTTG GGAGGTCATT TTAAGTTAGC TCCATGGTGA ACTGGATGAG | 40050 |
| GTTGTGATAA TCATAAGAAG GTGCCAAACC CTCAGATCAT GAGCCTTAGA | 40100 |
| GTTGAGAGAT TAAGCCTGGA AAGGGAAACT GCCCTTAACA GTTACTTTGG | 40150 |

-continued

```
GATTGTGGGT AAAGCAGAGA GAACCTGTGT CTGGAGGAGG AGTGGAAGAA           40200

TACAGTGCTC TCGTCCCAGG GCAGTCAAAC ACAGTGCACA AACTAGTTGT           40250

TTTATGCACA TTGTCTCCAG AAAGTGTTTG AGAAATAAGG GTTATACTTC           40300

CTTGAGGTGA GATGCCAAGA AGCCACTAAG CTAACACTGT TTCCCTAAGC           40350

TT                                                              40352

(2) INFORMATION FOR SEQ ID NO: 16:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO: 16:

GATCATCCAG GAGTACAACT CGA                                          23

(2) INFORMATION FOR SEQ ID NO: 17:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 17:

CCCGAGCGAG CTTAAGGAGT                                              20

(2) INFORMATION FOR SEQ ID NO: 18:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO: 18:

AGCGAGTGTA GGGGGTGCG                                               19
```

ISOLATED PROTEIN MOLECULES WHICH ARE MEMBERS OF THE MAGE-B FAMILY

RELATED APPLICATIONS

This application is a divisional of Ser. No. 08/846,111 filed Apr. 25, 1997, now U.S. Pat. No. 6,017,705 which is a continuation-in-part of Ser. No. 08/658,578, filed Jun. 5, 1996, now U.S. Pat. No. 5,759,783 which is a continuation-in-part of Ser. No. 08/403,388, filed Mar. 14, 1995, now U.S. Pat. No. 5,587,289 both of which are incorporated by reference.

FIELD OF THE INVENTION

This invention relates to a nucleic acid molecule which codes for a tumor rejection antigen precursor. More particularly, the invention concerns genes, whose tumor rejection antigen precursor is processed, inter alia, into at least one tumor rejection antigen. The tumor rejection antigen precursors in question do not appear to be closely related to other known tumor rejection antigen precursor coding sequences, and were isolated from the Xp region of human X chromosomes, in contrast to the genes to which they are most closely related, which were found on the Xq region. These newly isolated genes are members of the MAGE-B family, while those in the Xq region are now considered to be members of the MAGE-A family.

BACKGROUND AND PRIOR ART

The process by which the mammalian immune system recognizes and reacts to foreign or alien materials is a complex one. An important facet of the system is the T lymphocyte, or "T cell" response. This response requires that T cells recognize and interact with complexes of cell surface molecules, referred to as human leukocyte antigens ("HLA"), or major histocompatibility complexes ("MHCs"), and peptides. The peptides are derived from larger molecules which are processed by the cells which also present the HLA/MHC molecule. See in this regard Male et al., Advanced Immunology (J. P. Lipincott Company, 1987), especially chapters 6–10. The interaction of T cells and HLA/peptide complexes is restricted, requiring a T cell specific for a particular combination of an HLA molecule and a peptide. If a specific T cell is not present, there is no T cell response even if its partner complex is present. Similarly, there is no response if the specific complex is absent, but the T cell is present. This mechanism is involved in the immune system's response to foreign materials, in autoimmune pathologies, and in responses to cellular abnormalities. Much work has focused on the mechanisms by which proteins are processed into the HLA binding peptides. See, in this regard, Barinaga, Science 257: 880 (1992); Fremont et al., Science 257: 919 (1992); Matsumura et al., Science 257: 927 (1992); Latron et al., Science 257: 964 (1992).

The mechanism by which T cells recognize cellular abnormalities has also been implicated in cancer. For example, in PCT application PCT/US92/04354, filed May 22, 1992, published on Nov. 26, 1992, and incorporated by reference, a family of genes is disclosed, which are processed into peptides which, in turn, are expressed on cell surfaces, which can lead to lysis of the tumor cells by specific CTLs cytolytic T lymphocytes, or "CTLs" hereafter. The genes are said to code for "tumor rejection antigen precursors" or "TRAP" molecules, and the peptides derived therefrom are referred to as "tumor rejection antigens" or "TRAs". See Traversari et al., Immunogenetics 35: 145 (1992); van der Bruggen et al., Science 254: 1643 (1991), for further information on this family of genes. Also, see U.S. patent application Ser. No. 807,043, filed Dec. 12, 1991, now U.S. Pat. No. 5,342,774, incorporated by reference in its entirety. The "MAGE" family of tumor rejection antigen precursors is disclosed in this patent.

In U.S. patent application Ser. No. 938,334, now U.S. Pat. No. 5,405,940, Apr. 15, 1995, the disclosure of which is incorporated by reference, it is explained that the MAGE-1 gene codes for a tumor rejection antigen precursor which is processed to nonapeptides which are presented by the HLA-A1 molecule. The nonapeptides which bind to HLA-A1 follow a "rule" for binding in that a motif is satisfied. In this regard, see e.g. PCT/US93/07421; Falk et al., Nature 351: 290–296 (1991); Engelhard, Ann Rev. Immunol. 12: 181–207 (1994); Ruppert et al., Cell 74: 929–937 (1993); R ötzschke et al., Nature 348: 252–254 (1990); Bjorkman et al., Nature 329: 512–518 (1987); Traversari et al., J. Exp. Med. 176: 1453–1457 (1992). The references teach that given the known specificity of particular peptides for particular HLA molecules, one should expect a particular peptide to bind to one HLA molecule, but not to others. This is important, because different individuals possess different HLA phenotypes. As a result, while identification of a particular peptide as being a partner for a specific HLA molecule has diagnostic and therapeutic ramifications, these are only relevant for individuals with that particular HLA phenotype. There is a need for further work in the area, because cellular abnormalities are not restricted to one particular HLA phenotype, and targeted therapy requires some knowledge of the phenotype of the abnormal cells at issue.

In U.S. patent application Ser. No. 08/008,446, filed Jan. 22, 1993 now abandoned and incorporated by reference, the fact that the MAGE-1 expression product is processed to a second TRA is disclosed. This second TRA is presented by HLA-Cw*1601 molecules. The disclosure shows that a given TRAP can yield a plurality of TRAs, each of which will satisfy a motif rule for binding to an MHC molecule.

In U.S. patent application Ser. No. 994,928, filed Dec. 22, 1992, now abandoned and incorporated by reference herein teaches that tyrosinase, a molecule which is produced by some normal cells (e.g., melanocytes), is processed in tumor cells to yield peptides presented by HLA-A2 molecules.

In U.S.; patent application Ser. No. 08/032,978, filed Mar. 18, 1993, now U.S. Pat. No. 5,620,886 and incorporated by reference in its entirety, a second TRA, not derived from tyrosinase is taught to be presented by HLA-A2 molecules. The TRA is derived from a TRAP, but is coded for by a non-MAGE gene. This disclosure shows that a particular HLA molecule may present TRAs derived from different sources.

In U.S. patent application Ser. No.08/079,110, filed Jun. 17, 1993 and incorporated by reference herein, an unrelated tumor rejection antigen precursor, the so-called "BAGE" precursor is described. The BAGE precursor is not related to the MAGE family.

In U.S. patent applications Ser. No. 08/096,039 now abandoned and Ser. No. 08/250,162, now U.S. Pat. No. 5,610,013 both of which are incorporated by reference, non-related TRAP precursor GAGE is also disclosed.

The work which is presented by the papers, patent, and patent applications cited supra deal, in large part, with the MAGE family of genes, and the unrelated BAGE, GAGE and DAGE genes, showing that there are different, additional tumor rejection antigen precursors expressed by cells.

It has now been found that there is yet another family of tumor rejection antigen precursor genes. These nucleic acid molecules show homology to the MAGE family of genes, but this homology is insufficient to identify the members of the MAGE-B family by hybridization with the members of the MAGE-A family, as set forth in, e.g., PCT Application PCT/US92/04354 and U.S. Pat. No. 5,342,774, under the conditions of stringency set forth therein. Further, the isolated nucleic acid molecules of the invention were all found on the Xp arm of the X chromosome, as contrasted to the previously identified members of the MAGE-A family, all of which were found on the Xq arm. Thus, the invention relates to isolated nucleic acid molecules which encode for MAGE-B tumor rejection antigen precursors and the uses thereof.

The invention is explained in further detail in the disclosure which follows.

DETAILED DESCRIPTION OF PREFERRED EMBODIMENTS

EXAMPLE 1

The cosmids D5 and 4965 have been described by Muscatelli, et al., Nature 372: 672–676 (1994), as well as in Muscatelli, et al., Proc. Natl. Acad. Sci. USA 92: 4987–4991 (1995) the disclosures of which are incorporated by reference. These cosmids contain portions of the Xp arm of the X-chromosome. The cosmids were digested, using restriction endonucleases EcoRI, BamHI, Hind III, and PstI. Once digested, the DNA was transferred, to a nylon membrane, following agarose electrophoretic migration in an agarose gel.

Following this, a probe, based upon SEQ ID NO: 1, i.e., the sequence for Xp1, was used in hybridization experiments. The probe was approximately 0.45 kilobases in length, and contains 41 base pairs of the first exon (73 base pairs total), the complete second exon, and 299 base pairs of the third (1603 base pairs total). The sequence for what is referred to herein as "MAGE-B1" and is referred to elsewhere as "Xp" may be found in Muscatelli, et al., Proc. Natl. Acad. Sci. USA supra. Further the sequence is found in the EMBL sequence data bank reference to accession number emb X82539, available no later than Feb. 7, 1995.

In order to prepare the 0.4 kb probe, the following primers, i.e., SEQ ID NO: 11 and SEQ ID NO: 12 were used, in PCR, on B1 cDNA:

5'-GTGGTGTCCAGCAGTGTCTC-3'
5'-GTCAGATTCGGTACATGACACAG-3

Specifically, the DNA was denatured with NaOH and neutralized in the gel before transfer to a nylon membrane using 20×SSC (SSC=0.15M NaCl, 0.015 M sodium citrate, pH 7). Following transfer, the membranes were rinsed for 5 minutes in 6×SSC at room temperature, baked for one hour at 80° C., and pretreated for 4 hours in 6×SSC, 10×Denhardt's solution (0.02% Ficoll, 0.02% polyvinylpyrrolidone, 0.02% BSA), at 65° C.

The membrane was then hybridized in 3.5×SSC, 1×Denhardt's Solution, 25 mm sodium phosphate buffer (pH 7.0), 0.5% SDS, 2 mM EDTA and $3 \times 10^6$ cpm/ml α $^{32}$P-CTP radiolabelled probe. Hybridization was performed for 18 hours at 65° C. The membrane was then washed at 65° C., four times, for one hour each time in 2×SSC, 0.5% SDS, 1×Denhardt's solution; once for 30 minutes at 0.2×SSC, 0.1% SDS; and once for 30 minutes in 0.1×SSC, 0.1% SDS. The membranes were autoradiographed using Kodak X-ARS film, and Kodak X-Omatic fine intensifying screens.

Following the hybridization, several signals of differing intensity were observed. Of these, three EcoRI fragments from cosmid 4965, which were 1.5, 2.2, and 2.5 kilobases in length were isolated, and cloned into vector pTZ19R for sequencing. Partial sequencing showed that each fragment contained a sequence homologous to the third exon of B1. Homology of the three sequences, relative to B1, was 75%, 60%, and 80%, for genes referred to hereafter as MAGE-B2, MAGE-B3, and MAGE-B4. These are presented in SEQ ID NOS: 2, 3 and 4, respectively.

The foregoing disclosure, places many tools of extreme value in the hands of the skilled artisan. To begin, the examples identify isolated nucleic acid molecules which code for MAGE-B tumor rejection antigen precursors as well as the nucleic acid molecules complementary thereto. It is known that DNA exists in double stranded form, and that each of the two strands is complementary to the other. Nucleic acid hybridization technology has developed to the point where, given a strand of DNA, the skilled artisan can isolate its complement, or synthesize it. The invention includes, inter alia, the phenomenon of double strandedness to permit the artisan to identify the X chromosome, especially the Xp element, as well as defects in the chromosome.

Such assays can be carried out by one of ordinary skill in the art, using standard methodologies. For example, using the well known polymerase chain reaction (PCR), one uses the following primers:

For identifying B2:
5'-TAAAAAAGGTGCCAAGAGCCAC-3' (SEQ ID NO: 5);
5'-TGAGGCCCTCAGAGGCTTTC-3' (SEQ ID NO: 6).

For identifying B3:
5'-AGTCTGCTGGTAGGTCACGTA-3' (SEQ ID NO: 7);
5'-TCAGGAACTGCACCAACATATTT-3'(SEQ ID NO: 8).

For identifying B4:
5'-AGGGATACTGCCTCCAGCTC-3' (SEQ ID NO: 9);
5'-CAGGAACTGCACTAACATCTTC-3' (SEQ ID NO: 10).

Example 2, which follows, shows one way this can be done.

EXAMPLE 2

The primers of SEQ ID NO: 5 and SEQ ID NO: 6 were used, for example, to determine whether or not MAGE-B2 was expressed in tumors.

Total cellular RNA was extracted from tumor cell samples, using the well known guanidine-isothiocyanate/cesium chloride methodology, (see, e.g., Davis et al., Basic Methods in Molecular Elsevier, NY (1986), pp. 130–135, which is not repeated here. Next, cDNA was synthesized, using 2 ug total RNA from the samples. Synthesis was carried out by extension with oligo dT(15), in a 20 µl reaction volume, in accordance with DeSmet et al, Immunogenetics 39: 121–129 (1994), incorporated by reference. After incubation for one hour at 42° C., the cDNA reaction mixture was diluted with water to 100 µl. PCR was then carried out using SEQ ID NOS: 5 and 6. Each PCR reaction was carried out, using 5 µl of cDNA (which corresponds to 100 ng of RNA), supplemented with 5 µl of 10×PCR buffer, and 1 µl of each variety of dNTP (10 mM), 0.5 µl each of 80 µM solutions of primers, 1.25 units of AmpliTaq DNA polymerase and water, to a total volume of 50 µl. This mixture was then heated to 94° C. for five minutes, followed by amplification in a thermal cycler for 30 cycles (one minute at 94° C., two minutes at 63° C., two minutes at 72°

C.). Cycling was then concluded with a final extension step (15 minutes, 72° C.). A 10 μl sample of each reaction was run on 1% agarose gel, and visualized using ethidium bromide fluorescence.

RNA integrity was verified, and samples containing strongly degraded RNA excluded, by carrying out a 20 cycle PCR assay, using primers specific for β-actin, in accordance with Weynants et al, Int. J. Cancer 56: 826–829 (1994) incorporated by reference.

The results for tumors follow. The first column is the number of tumor samples tested, the second is the number which were positive for MAGE-B2:

| Testicular seminoma | 6 | 5 |
| Non-small cell lung carcinoma | 20 | 6 |
| Melanoma | 26 | 5 |
| Breast | 10 | 2 |
| Sarcoma | 10 | 1 |
| Leukemia | 10 | 1 |

With the exception of the positive leukemia, any tumor sample which was positive for MAGE-B2 was also positive for at least one MAGE-Xq.

Expression of MAGE-B2 was found in fetal and adult testis, but was not found in any normal kidney, liver, adrenal gland, skin, breast, brain, heart, ovary, prostate, cerebellum, peripheral blood lymphocyte, colon, stomach, lung, bladder, bone marrow or endometrium cells.

EXAMPLE 3

Additional experiments were carried out on cosmids D5 and 4965, which are discussed in example 1, supra. Specifically cDNA as disclosed by Muscatelli, et al, Proc. Natl. Acad. Sci USA 92:4987–4991 (1995), was subjected to PCR amplification. In these amplifications, the primers:

5'- GTGGTGTCCA GCAGTGTCT C -3' (SEQ ID NO:11) and

SEQ ID NO:12 were used, to generate a 0.45 kb probe. A second probe was then prepared using:

5'- AAT GTG TTG GGA GCC TAT GAT -3' (SEQ ID NO:13) and

5'- ATT ATG TTG TGT GAG GTT CTT TCA -3' (SEQ ID NO:14) to generate a 726 base pair probe.

The first probe contained 41 bp of exon 1, 105 bp of exon 2, and 300 bp of exon 3 of MAGE-B1, while the second probe consisted of the 726 bp at the 3'-end of exon 4.

Southern blotting was then carried out on both cosmids, using standard methods as can be found in, e.g., Lurquin, et al, Cell 58:293–303 (1989). Any fragments of the cosmids which hybridized with the probes were cloned into commercially available vectors (ethyl pTZ18R or pTZ19R), and then sequenced.

The results of this work identified three sequences which showed significant identity to the last exon of MAGE-B1, as reported by Muscalelli, et al, supra. One sequence was identical to MAGE-B2, as described in Lurquin, et al, U.S. Pat. No. 5,587,289, as MAGE-Xp2, and by Dabovic, et al, Mamm. Genome 6:571–580 (1995), as "DAM 6". This meant that there were two other homologous genes present in the cosmids.

EXAMPLE 4

In order to determine the precise positions, and complete sequences of the positives described supra, the portion of the Xp arm of the X chromosome, found in cosmids D5 and 4965, that includes the sequences of these hybridizing fragments was sequenced by "chromosome walking" (as described in Molecular Biology of the Cell, Alberts et al., Second Edition p.262–265).

A total of 40,352 kb was sequenced and this complete sequence is set out in SEQ ID NO:15. No further sequencing was carried out after this 40.352 kb sequence has been obtained because the start site and 5' UTR of MAGE-B2 was at the 5' end of this 40.352 kb sequence and the stop condon and poly-A signal of MAGE-B1 was located at the 3' end of this 40.352 kb sequence. At this point it was clear that all of the Xp hybridizing fragments from the Southern analysis (described in Example 3) were located within this 40,352 kb sequence obviating the need for any further sequencing.

When the sequence information obtained in example 3 was compared to the full, 40,352 bases of SEQ ID NO:15, the following was discovered:

| GENE | POSITION IN SEQ ID NO: 15 |
|---|---|
| B2 | 3266–7791 |
| B3 | 23545–25193 |
| B4 | 29747–31473 |
| B1 | 31402–39690 |

Within these sequences, further analyses showed that B2 contains two exons, at nucleotides 3266–3364, and 6278–7979, respectfully. The entire coding region is found at nucleotides 6283–7242, with a poly A signal being found at nucleotides 7772–7777.

As to the B3 gene, a single coding exon, at nucleotides 23545–25193 was found. The coding region consisted of nucleotides 23606–24646, with a poly-A signal at nucleotides 25151–25156.

The gene for B4 is thought to extend through to poly-A signal at 31821–31826, with the coding sequence being found at nucleotides 29807–30847.

The MAGE-B1 gene is the most complex of the four. The first exon, at nucleotides 31402–31473, is within the MAGE-B4 coding exon. Exons 2, 3 and 4 are found at nucleotides 33957–39690, i.e., at 33957–34061, 35057–35139, and 38087–39690, respectively. The coding sequence is found completely within the fourth exon, i.e., at nucleotides 38147–39190. The poly-A signal is at 39673–39678.

EXAMPLE 5

Comparison of the nucleotides in these sequences and other known tumor rejection antigen precursors, is set forth in Table 1, which follows. It can be seen that MAGE-B1, B2 and B4 form a closely related set, with about 80% identity while MAGE-B3 is about 70% identical with the others.

Further comparison reveals protein encoding regions corresponding to 347, 319, 346, and 346 amino acids for the MAGE-D proteins. These show anywhere from 49–68% identity.

TABLE 1

Sequence comparison of the human and mouse MAGE coding regions and proteins

| | A1 | A2 | A3 | A4 | A5 | A6 | A7 | A8 | A9 | A10 | A11 | A12 | B1 | B2 | B3 | B4 | sB1 | sB2 | sB3 |
|---|---|---|---|---|---|---|---|---|---|---|---|---|---|---|---|---|---|---|---|
| | | | | | | | | % Nucleotide Identity | | | | | | | | | | | |
| MAGE-A1 | 100 | 80 | 81 | 84 | 81 | 81 | 84 | 77 | 76 | 69 | 75 | 81 | 62 | 69 | 61 | 60 | 58 | 57 | 56 |
| MAGE-A2 | 80 | 100 | 92 | 82 | 82 | 92 | 81 | 78 | 74 | 65 | 73 | 83 | 59 | 60 | 59 | 61 | 55 | 58 | 56 |
| MAGE-A3 | 81 | 92 | 100 | 82 | 86 | 98 | 80 | 76 | 78 | 66 | 75 | 92 | 51 | 61 | 60 | 82 | 54 | 54 | 54 |
| MAGE-A4 | 84 | 82 | 82 | 100 | 87 | 83 | 84 | 79 | 79 | 69 | 77 | 83 | 83 | 61 | 61 | 62 | 57 | 57 | 57 |
| MAGE-A5 | 81 | 82 | 65 | 87 | 100 | 86 | 74 | 77 | 73 | 60 | 74 | 84 | 50 | 45 | 52 | 47 | 51 | 51 | 55 |
| MAGE-A6 | 81 | 92 | 98 | 83 | 86 | 100 | 80 | 778 | 76 | 58 | 75 | 92 | 61 | 61 | 60 | 61 | 64 | 64 | 64 |
| MAGE-A7 | 84 | 81 | 80 | 84 | 74 | 80 | 100 | 83 | 87 | 79 | 79 | 81 | 54 | 56 | 54 | 82 | 48 | 48 | 45 |
| MAGE-A8 | 77 | 76 | 76 | 79 | 77 | 75 | 83 | 100 | 79 | 68 | 75 | 76 | 60 | 69 | 58 | 61 | 47 | 47 | 48 |
| MAGE-A9 | 76 | 74 | 76 | 70 | 73 | 78 | 87 | 79 | 100 | 69 | 78 | 77 | 62 | 59 | 61 | 63 | 67 | 57 | 55 |
| MAGE-A10 | 69 | 65 | 68 | 69 | 80 | 68 | 79 | 88 | 69 | 100 | 72 | 68 | 60 | 80 | 62 | 63 | 68 | 68 | 68 |
| MAGE-A11 | 75 | 73 | 75 | 77 | 74 | 75 | 79 | 76 | 76 | 72 | 100 | 75 | 62 | 62 | 62 | 83 | 69 | 58 | 58 |
| MAGE-A12 | 81 | 93 | 92 | 83 | 84 | 92 | 81 | 76 | 77 | 68 | 75 | 100 | 62 | 80 | 50 | 62 | 58 | 68 | 67 |
| MAGE-B1 | 82 | 59 | 61 | 63 | 60 | 61 | 54 | 60 | 62 | 80 | 92 | 62 | 100 | 80 | 88 | 81 | 63 | 63 | 63 |
| MAGE-B2 | 59 | 60 | 61 | 61 | 45 | 61 | 58 | 59 | 59 | 60 | 62 | 60 | 90 | 100 | 65 | 78 | 64 | 64 | 64 |
| MAGE-B3 | 81 | 59 | 60 | 81 | 62 | 80 | 54 | 56 | 61 | 62 | 62 | 50 | 88 | 86 | 100 | 71 | 50 | 60 | 61 |
| MAGE-B4 | 50 | 61 | 82 | 62 | 47 | 61 | 62 | 61 | 63 | 63 | 83 | 52 | 81 | 76 | 71 | 100 | 81 | 51 | 51 |
| Smage-B1 | 58 | 55 | 54 | 57 | 51 | 54 | 48 | 47 | 57 | 58 | 59 | 55 | 53 | 64 | 80 | 81 | 100 | 99 | 98 |
| Smage-B2 | 57 | 55 | 54 | 57 | 51 | 54 | 48 | 47 | 57 | 58 | 58 | 58 | 63 | 64 | 60 | 61 | 99 | 100 | 98 |
| Smage-B3 | 60 | 56 | 54 | 67 | 55 | 54 | 45 | 45 | 58 | 58 | 68 | 57 | 63 | 64 | 61 | 61 | 98 | 98 | 100 |
| | | | | | | | | % Amino Acid Identity | | | | | | | | | | | |
| MAGE-A1 | 100 | 67 | 67 | 76 | 68 | 68 | 23 | 64 | 60 | 52 | 59 | 67 | 38 | 39 | 42 | 43 | 35 | 36 | 37 |
| MAGE-A2 | 67 | 100 | 84 | 87 | 59 | 54 | 18 | 62 | 69 | 46 | 58 | 88 | 39 | 35 | 35 | 40 | 33 | 33 | 33 |
| MAGE-A3 | 67 | 94 | 100 | 67 | 72 | 95 | 17 | 62 | 59 | 47 | 50 | 85 | 37 | 37 | 34 | 39 | 33 | 33 | 34 |
| MAGE-A4 | 75 | 67 | 67 | 100 | 78 | 87 | 23 | 66 | 64 | 51 | 62 | 67 | 42 | 39 | 41 | 41 | 38 | 38 | 39 |
| MAGE-A5 | 68 | 89 | 72 | 78 | 100 | 72 | 13 | 61 | 52 | 39 | 69 | 69 | 28 | 30 | 20 | 24 | 19 | 19 | 20 |
| MAGE-A6 | 68 | 84 | 96 | 87 | 72 | 100 | 18 | 82 | 68 | 49 | 80 | 84 | 37 | 37 | 35 | 40 | 34 | 34 | 34 |
| MAGE-A7 | 23 | 18 | 17 | 23 | 13 | 18 | 100 | 25 | 27 | 20 | 21 | 17 | 16 | 16 | 20 | 14 | 13 | 13 | 14 |
| MAGE-A8 | 64 | 82 | 62 | 66 | 81 | 82 | 25 | 100 | 66 | 54 | 80 | 84 | 38 | 35 | 36 | 38 | 29 | 29 | 29 |
| MAGE-A9 | 50 | 69 | 58 | 64 | 52 | 58 | 27 | 88 | 100 | 50 | 69 | 69 | 39 | 38 | 38 | 43 | 34 | 34 | 34 |
| MAGE-A10 | 52 | 45 | 47 | 51 | 39 | 49 | 20 | 54 | 60 | 100 | 50 | 45 | 41 | 38 | 41 | 47 | 35 | 35 | 35 |
| MAGE-A11 | 59 | 68 | 60 | 62 | 59 | 60 | 21 | 60 | 59 | 60 | 100 | 59 | 42 | 38 | 40 | 44 | 38 | 38 | 30 |
| MAGE-A12 | 67 | 88 | 85 | 87 | 59 | 84 | 17 | 64 | 59 | 45 | 59 | 100 | 39 | 37 | 35 | 40 | 33 | 33 | 34 |
| MAGE-B1 | 38 | 39 | 37 | 42 | 28 | 37 | 16 | 38 | 39 | 41 | 42 | 39 | 100 | 82 | 49 | 58 | 47 | 47 | 47 |
| MAGE-B2 | 39 | 38 | 37 | 39 | 30 | 37 | 15 | 35 | 38 | 38 | 38 | 37 | 82 | 100 | 49 | 83 | 48 | 48 | 47 |
| MAGE-B3 | 42 | 35 | 34 | 41 | 20 | 35 | 20 | 38 | 38 | 41 | 40 | 38 | 49 | 49 | 100 | 66 | 42 | 42 | 43 |
| MAGE-B4 | 43 | 40 | 39 | 41 | 24 | 40 | 14 | 38 | 43 | 47 | 44 | 40 | 68 | 83 | 55 | 100 | 82 | 52 | 61 |
| Smage-B1 | 36 | 33 | 33 | 38 | 19 | 34 | 15 | 29 | 34 | 36 | 38 | 33 | 47 | 48 | 42 | 52 | 100 | 100 | 97 |
| Smage-B2 | 36 | 33 | 33 | 38 | 19 | 34 | 13 | 29 | 34 | 36 | 38 | 33 | 47 | 48 | 42 | 52 | 100 | 100 | 97 |
| Smage-B3 | 37 | 33 | 34 | 38 | 20 | 34 | 14 | 29 | 34 | 35 | 30 | 34 | 47 | 47 | 43 | 61 | 97 | 97 | 100 |

EXAMPLE 6

In work reported by Muscatelli, et al, Proc. Natl. Acad. Sci. USA 92:4987–4991 (1995), MAGE-B1 from a cDNA library from testis was found to comprise two types, i.e., one included all four exons, and the other, exons 1, 2 and 4.

Experiments were carried out to verify this, using SEQ ID NOS: 11 and 12, set forth, supra, on a testis cDNA library, using RT-PCR. To carry this out, total cellular RNA was extracted, using the well known guanidine—isothiocyanate/cesium chloride method of, e.g., Davis, et al, *Basic Methods In Molecular Biology,* Elsevier Science Publishing Co., Inc., New York (1986). Samples (2 μg), of total RNA were used for cDNA synthesis, via extension of oligo dt(15), in 20 μl reaction volumes. See DeSmet, et al, Immunogenetics 39:121–129 (1996). The cDNA was incubated at 42° C., for 1 hour, and then diluted to 100 μl with water. The primers set forth, supra, were then combined with 5 μl of cDNA, together with 5 μl of 10×DNA polymerase buffer, 1 μl of each of 10 mM dNTP, ad 1 unit of .DNA polymerase. Water was added to a total volume of 50 μl. The mixture was heated to 94° C. for 5 minutes, followed by amplification for 30 cycles (a cycle: 1 minute 94° C., 2 minutes at 63° C., and an extension of 2 minutes at 72° C.). The cycling was concluded with a final extension step of 15 minutes at 72° C. Following this, a 10 μl sample of the reaction was run on a 1.5% agarose gel, and visualized by ethidium bromide fluorescence. RNA integrity was verified, and samples with strongly degraded RNA, were excluded by carrying out a PCR assay of 20 cycles, using B-actin specific primers.

The results verified the previous findings, that there were two types of transcript which were present. The transcript containing 4 exons was far less abundant than the other.

The pattern of amplification products using SEQ ID NO:17 and 12 was also determined using RT-PCR on a testis cDNA library. In addition to a species comprising all 4 exons, a major species containing exons 3 and 4 was obtained.

Eighty-four tumor samples and tumor cell lines of various histological types were found to be negative for MAGE-B1 expression when tested with primers whose sequences were located in the first and fourth exons (SEQ ID NOS:11 and 12). However, using primers whose sequences were located in the third and fourth exons (SEQ ID NOS:17 and 12), MAGE-BL expression was detected in samples from NSCLC and mammary carcinoma and tumors of other histological type patients.

EXAMPLE 7

The pattern of distribution of expression of the MAGE-B genes was studied, via RT-PCR.

The protocol set forth in example 5, supra, was followed with some changes, as indicated herein.

Various combinations of primers were used, based upon the MAGE-B sequences. In addition to SEQ ID NO: 11 and 12, presented supra, the following primers were used for MAGE-B1:

5'-GAT CAT CCA GGA GTA CAA CTC GA -3' (SEQ ID NO:16)

5'-CCC GAG CGA GCT TAA GGA GT -3' (SEQ ID NO:17)

SEQ ID NOS: 11, 16 and 17 are sense primers corresponding to 1, 2 and 3, respectively, of MAGE-B1. One of these was used in combination with SEQ ID NO:12, in assays for expression of MAGE-B1.

For MAGE-B2, one of 5'-AGC GAG TGT AGG GGG TGC G -3' (SEQ ID NO:18) or SEQ ID NO:15, supra, together with SEQ ID NO:6, supra, were used. SEQ ID NOS:5 and 18 are sense primers for exons 1 and 2 of MAGE-B2, while SEQ ID NO:6 is an antisense primer for exon 2.

As indicated, RT-PCR was carried out, essentially as in Example 5, with the following exceptions. Forty cycles were carried out for MAGE-B1, while MAGE-B2 was assayed using thirty cycles. The cycle parameters given in example 5, supra, was modified as follows. When SEQ ID NOS:17 and 12, and SEQ ID NO:18 and 6, were used, a cycle was 1 minute at 94° C., and 2 minutes at 68° C., followed by the two minute extension. When SEQ ID NOS: 16 and 12 were used, the two minutes was carried out at 65° C.

The results are set forth in Table 2, which follows:

|  | MAGE-B1 LUR171-1338 40 cycles | MAGE-B2 LUR84-LUR85 and/or LUR162-LUR85 30 cycles |
|---|---|---|
| Surgical tumor samples |  |  |
| Colorectal carcinoma | 0/12 | 0/12 |
| Gastric carcinoma | 0/2 | 0/2 |
| Leukemia | 0/48 | 1/50 |
| Lymphoma | 0/3 | 1/3 |
| Myeloma | 0/1 | 0/1 |
| Melanoma | 8/38 | 8/37 |
| Skin carcinoma | 1/4 | 0/4 |
| Naevus (benign lesion) | 0/6 | 0/6 |
| Brain tumor | 0/8 | 0/8 |
| Neuroblastoma | 0/2 | 0/2 |
| Head and neck squamous cell carcinoma | 0/12 | 2/12 |
| Pleural mesothelloma | 0/3 | 0/3 |
| Small cell lung carcinoma | 0/1 | 0/1 |
| Non-small cell lung carcinoma | 4/29 | 13/29 |
| Sarcoma | 1/11 | 2/11 |
| Mammary carcinoma | 2/12 | 3/12 |
| Prostate adenocarcinoma | 0/6 | 0/6 |
| Testicular tumor | 8/9 | 8/9 |
| Renal cell carcinoma | 0/11 | 0/11 |
| Bladder carcinoma | 0/12 | 0/12 |
| Cell lines |  |  |
| Colorectal carcinoma | 0/6 | 0/5 |
| Leukemia | 0/3 | 0/3 |
| EBV transformed B lymphoctyes | 0/1 | 0/1 |
| Melanoma | 2/9 | 3/9 |
| Small cell lung carcinoma | 0/2 | 1/2 |
| Non small cell lung carcinoma | 0/8 | 3/6 |
| Sarcoma | 0/2 | 0/2 |
| Normal tissues |  |  |
| Colon | 0/1 | 0/1 |
| Stomach | 0/1 | 0/1 |
| Liver | 0/1 | 0/1 |
| Bone marrow | 0/1 | 0/1 |
| Peripheral blood lymphocytes | 0/1 | 0/1 |
| Thymocytes | 0/1 | 0/1 |
| Skin | 0/1 | 0/1 |
| Brain | 0/2 | 0/2 |
| Cerebellum | 0/1 | 0/1 |
| Heart | 0/1 | 0/1 |
| Lung | 0/1 | 0/1 |
| Breast | 0/2 | 0/2 |
| Ovary | 0/1 | 0/1 |
| Uterus | 0/2 | 0/2 |
| Prostate | 0/1 | 0/1 |
| Testis | 2/2 | 2/2 |
| Adrenal gland | 0/1 | 0/1 |
| Kidney | 0/1 | 0/1 |
| Bladder | 0/1 | 0/1 |
| Fetal tissues: |  |  |
| liver | 0/1 | 0/1 |
| brain | 0/1 | 0/1 |
| testis | 1/1 | 1/1 |
| placenta | 0/1 | 1/1 |

Note that, in this table and the table which follows "LUR 171" is SEQ ID NO:17, "1338" is SEQ ID NO:12, "1339" is SEQ ID NO:11, "LUR 162" is SEQ ID NO:18, "LUR 84" is SEQ ID NO:5 and "LUR 85" is SEQ ID NO:6.

EXAMPLE 8

It is known that certain MAGE genes are inducible with 5-aza-2'-deoxycytidine, in both melanoma cells, and in different cell types which do not normally express the genes. See Weber, et al, Cancer Res 54:1766–1771 (1994); DeSmet, et al, Proc. Natl. Acad Sci. USA 93:7149–7153 (1996) ; DePlaen, et al, Genomics 40: (1997). Additional agents may also be used to induce MAGE genes.

In order to determine if the MAGE-1 genes parallel other genes in terms of inducibility, different types of cells were incubated for 72 hours in culture medium containing 1 $\mu$m 5-aza-2'-deoxycytidine ("DAC" hereafter), in accordance with DeSmet, et al, supra. The table which follows sets forth the result.

|  | MAGE-B1 | | | | MAGE-B2 | |
|---|---|---|---|---|---|---|
|  | LUR171–1338 (exon3–exon4) | | 1339–1338 (exon1–exon4) | | LUR162–LUR85 (exon1–exon2) | |
|  | – | +DAC | – | +DAC | – | +DAC |
| Cell lines: |  |  |  |  |  |  |
| MZ2-MEL | – | + | – | – | – | + |
| SK23-MEL | – | – | – | – | – | – |
| M1666/2-MEL | – | + | – | – | – | + |
| LE92.11-RCC | – | – | – | – | – | + |
| JAR | – | + | – | – | – | + |
| LB23-SAR | – | + | – | – | – | + |
| B-EBV | – | + | – | – | – | + |

-continued

| | MAGE-B1 | | | | MAGE-B2 | |
|---|---|---|---|---|---|---|
| | LUR171–1338 (exon3–exon4) | | 1339–1338 (exon1–exon4) | | LUR162–LUR85 (exon1–exon2) | |
| | – | +DAC | – | +DAC | – | +DAC |
| Normal tissues: | | | | | | |
| PBL-PHA | – | + | – | – | – | + |
| Fibroblasts | – | – | – | – | – | + |
| Dentritic cells | – | + | – | – | – | + |

"Nucleic acid molecule" as used herein refers to all species of DNA and RNA which possess the properties discussed supra. Genomic ("gDNA") and complementary DNA, or "cDNA" both code for particular proteins, and as the examples directed to isolation of MAGE coding sequences show, this disclosure teaches the artisan how to secure both of these.

The four MAGE-B genes are spread over 40,352 kb in the 160 kb X-linked critical region defined for the DSS (Dosage Sensitive Sex reversal) locus involved in sex determination (Bardoni et al. Nature Genetics 7:497–501 (1994)). This region is duplicated in patients with a male-to-female sex reversal phenotype. Genes in this region may be involved in X-linked disorders such as adrenal hypoplasis congenita and hypogonadism.

All isolated nucleic acid molecules which encode MAGE-B proteins, with the exception of MAGE-B1, are encompassed by this invention. This includes those nucleic acid molecules which hybridize to any of MAGE-B2, MAGE-B3, or MAGE-B4 under stringent conditions. As used herein, this refers to conditions such as hybridization with $5 \times 10^6$ cpm/ml for 18 hours at 65° C., followed by 4, 20 minute washes at 65° C., with each wash using 2×SSC, 0.5% SDS and 1×Denhardt's solution, followed by two washes at 0.2×SSC, 1% SDS (20 minutes, each wash), and, finally, two washes at 68° C., 1% SDS, a varying concentration of SSC, each of these washes being for 20 minutes. The final concentration of SSC should be no greater than 0.5×SSC, more preferably it is 0.2×SSC, and most preferably it is 0.1×SSC.

Similarly, RNA molecules, such as mRNA can be secured. Again, with reference to the skilled artisan, once one has a coding sequence in hand, mRNA can be isolated or synthesized.

Complementary sequences which do not code for TRAPs, such as "antisense DNA" or mRNA are useful, e.g., in probing for the coding sequence as well as in methodologies for blocking its expression.

It will also be clear that one may manufacture biologically pure cultures of prokaryotic and eukaryotic cell lines which have been transformed or transfected with nucleic acid sequences which code for or express the MAGE-B molecules. Such cultures can be used as a source for tumor rejection antigens, e.g., or as therapeutics. This aspect of the invention is discussed infra.

Cells transfected with MAGE-B coding sequences may also be transfected with other coding sequences. Examples of other coding sequences include cytokine genes, such as interleukins (e.g., IL-2 or IL-4), or major histocompatibility complex (MHC) or human leukocyte antigen (HLA) molecules. Cytokine gene transfection is of value because expression of these is expected to enhance the therapeutic efficacy of the biologically pure culture of the cells in vivo. The art is well aware of therapies where interleukin transfectants have been administered to subjects for treating cancerous conditions. In a particularly preferred embodiment, cells are transfected with sequence coding for each of (i) MAGE-Xp molecule, (ii) an HLA/MHC molecule, and (iii) a cytokine.

Transfection with an MHC/HLA coding sequence is desirable because certain of the TRAs derived from MAGE-B may be preferentially or especially presented only by particular MHC/HLA molecules. Thus, where a recipient cell already expresses the MHC/HLA molecule associated with presentation of a TRA, additional transfection may not be necessary although further transformation could be used to cause overexpression of the antigen. On the other hand, it may be desirable to transfect with a second sequence when the recipient cell does not normally express the relevant MHC/HLA molecule. It is to be understood, of course, that transfection with one additional sequence does not preclude further transfection with other sequences.

The term "biologically pure" as used in connection with the cell line described herein simply means that these are essentially free of other cells. Strictly speaking, a "cell line" by definition is "biologically pure", but the recitation will establish this fully.

Transfection of cells requires that an appropriate vector be used. Thus, the invention encompasses expression vectors where a coding sequence for the MAGE-Xp TRAP of interest is operably linked to a promoter. The promoter may be a strong promoter, such as those well known to the art, or a differential promoter, i.e., one which is operative only in specific cell types. The expression vectors may also contain all or a part of a viral or bacterial genome, such as vaccinia virus or BCG. Such vectors are especially useful in preparing vaccines.

The expression vectors may incorporate several coding sequences, as long as the MAGE-B sequence is contained therein. The cytokine and/or HLA genes discussed supra may be included in a single vector with the TRAP sequence. Where this is not desired, then an expression system may be provided, where two or more separate vectors are used where each coding sequence is operably linked to a promoter. Again, the promoter may be a strong or differential promoter. Co-transfection is a well known technique, and the artisan in this field is expected to have this technology available for utilization. The vectors may be constructed so that they code for the TRA molecule directly, rather than the MAGE-Xp TRAP. This eliminates the need for post-translational processing.

As the foregoing discussion makes clear, the sequences code for "tumor rejection antigen precursors" ("TRAPs") which, in turn, are processed into tumor rejection antigens ("TRAs"). Perhaps their most noteworthy aspect is as vaccines for treating various cancerous conditions. The evidence points to presentation of TRAs on tumor cells, followed by the development of an immune response and deletion of the cells. The evidence in the art shows that when various TRAs are administered to cells, a CTL response is mounted and presenting cells are deleted. This is behavior characteristic of vaccines, and hence TRAPs, which are processed into TRAs, and the TRAs themselves may be used, either alone or in pharmaceutically appropriate compositions, as vaccines. Similarly, presenting cells may be used in the same manner, either alone or as combined with ingredients or yield pharmaceutical compositions. Additional materials which may be used as vaccines include isolated cells which present the TRA molecule on their surface, as well as TRAP fragments, mutated viruses, especially etiolated forms, and transformed bacteria. "Fragments" as used herein refers to peptides which are smaller than the TRA, but which possess the properties required of a vaccine, as discussed supra. Another vaccine comprises or consists of complexes of TRA and HLA molecule. Vaccines of the type described herein may be used preventively, i.e., via administration to a subject in an amount sufficient to prevent onset of a cancerous condition.

The generation of an immune response, be it T-cell or B-cell related, is characteristic of the effect of the presented tumor rejection antigen. With respect to the B-cell response, this involves, inter alia, the generation of antibodies to the TRA, i.e., which specifically bind thereto. In addition, the TRAP molecules are of sufficient size to render them immunogenic, and antibodies which specifically bind thereto are a part of this invention. These antibodies may be polyclonal or monoclonal, the latter being prepared by any of the well recognized methodologies for their preparation which need not be repeated here. For example, mAbs may be prepared using an animal model, e.g., a Balb/C mouse or in a test tube, using, e.g., EBV transformants. In addition, antiserum may be isolated from a subject afflicted with a cancerous condition where certain cells present a TRA. Such antibodies may also be generated to epitope defined by the inter-action of TRA and HLA/MHC molecules.

Review of the foregoing disclosure will show that there are a number of facets to the system which may be referred to as "tumor rejection antigen presentation and recognition". Recognition of these phenomena has diagnostic consequences. For example, the existence of specific CTL clones, or antibodies to the TRA makes it possible to diagnose or monitor cancerous conditions (explained infra), by monitoring the CTLs in a sample from a subject, binding of antibodies to TRAs, or the activity of anti-TRA CTLs in connection with subject samples. Similarly, the expression of nucleic acid molecules for TRAPs can be monitored via amplification (e.g., "polymerase chain reaction"), anti-sense hybridization, probe technologies, and so forth. Various subject samples, including body fluids (blood, serum, and other exudates, e.g.), tissues and tumors may be so assayed.

A particular manner of diagnosis is to use an adaptation of the standard "tuberculin test" currently used for diagnosis of tuberculosis. This standard skin test administers a stable form of "purified protein derivative" or "PPD" as a diagnostic aid. In a parallel fashion, TRAs in accordance with this invention may be used in such a skin test as a diagnostic aid or monitoring method.

The term "cancerous condition" is used herein to embrace all physiological events that commence with the initiation of the cancer and result in final clinical manifestation. Tumors do not spring up "ab initio" as visible tumors; rather there are various events associated with the transformation of a normal cell to malignancy, followed by development of a growth of biomass, such as a tumor, metastasis, etc. In addition, remission may be conceived of as part of "a cancerous condition" as tumors seldom spontaneously disappear. The diagnostic aspects of this invention include all events involved in carcinogenesis, from the first transformation to malignancy of a single cell, through tumor development and metastasis, as well as remission. All are embraced herein.

Where "subject" is used, the term embraces any species which can be afflicted with a cancerous condition. This includes humans and non-humans, such as domesticated animals, breeding stock, and so forth.

There are therapeutic aspects of this invention as well. The efficacy of administration of effective amounts of TRAPs and TRAs as vaccines have already been discussed supra. Similarly, one may develop the specific CTLs in vitro and then administer these to the subject. Antibodies may be administered, either polyclonal or monoclonal, which specifically bind to cells presenting the TRA of interest. These antibodies may be coupled to specific antitumor agents, including, but not being limited to, methotrexate radioiodinated compounds, toxins such as ricin, other cytostatic or cytolytic drugs, and so forth. Thus, "targeted" antibody therapy is included herein, as is the application of deletion of the cancerous cells by the use of CTLs.

The terms and expression which have been employed are used as terms of description and not of limitation, and there is no intention in the use of such terms and expression of excluding any equivalents of the features shown and described or portions thereof, it being recognized that various modifications are possible within the scope of the invention.

What is claimed is:

1. An isolated protein encoded by a nucleic acid molecule which comprises the nucleotide sequence of SEQ ID NO: 2, 3, or 4.

2. The isolated protein of claim 1, wherein said nucleic acid molecule comprises SEQ ID NO: 2.

3. The isolated protein of claim 1, wherein said nucleic acid molecule comprises SEQ ID NO: 3.

4. The isolated protein of claim 1, wherein said nucleic acid molecule comprises SEQ ID NO: 4.

5. A composition comprising the isolated protein of claim 1, and at least one pharmaceutically acceptable ingredient.

6. An isolated protein which is encoded by a nucleic acid molecule having a nucleotide sequence selected from the group consisting of nucleotides 6283–7242 of SEQ ID NO: 15, nucleotides 23606–24646 of SEQ ID NO; 15, and nucleotides 29807–30847 of SEQ ID NO: 15.

7. An isolated protein which is encoded by a nucleic acid molecule having a nucleotide sequence selected from the group consisting of nucleotides 3266–7791 of SEQ ID NO: 15, nucleotides 23545–25193 of SEQ ID NO: 15, and nucleotide 29747–31473 of SEQ ID NO: 15.

* * * * *